Figure 1:
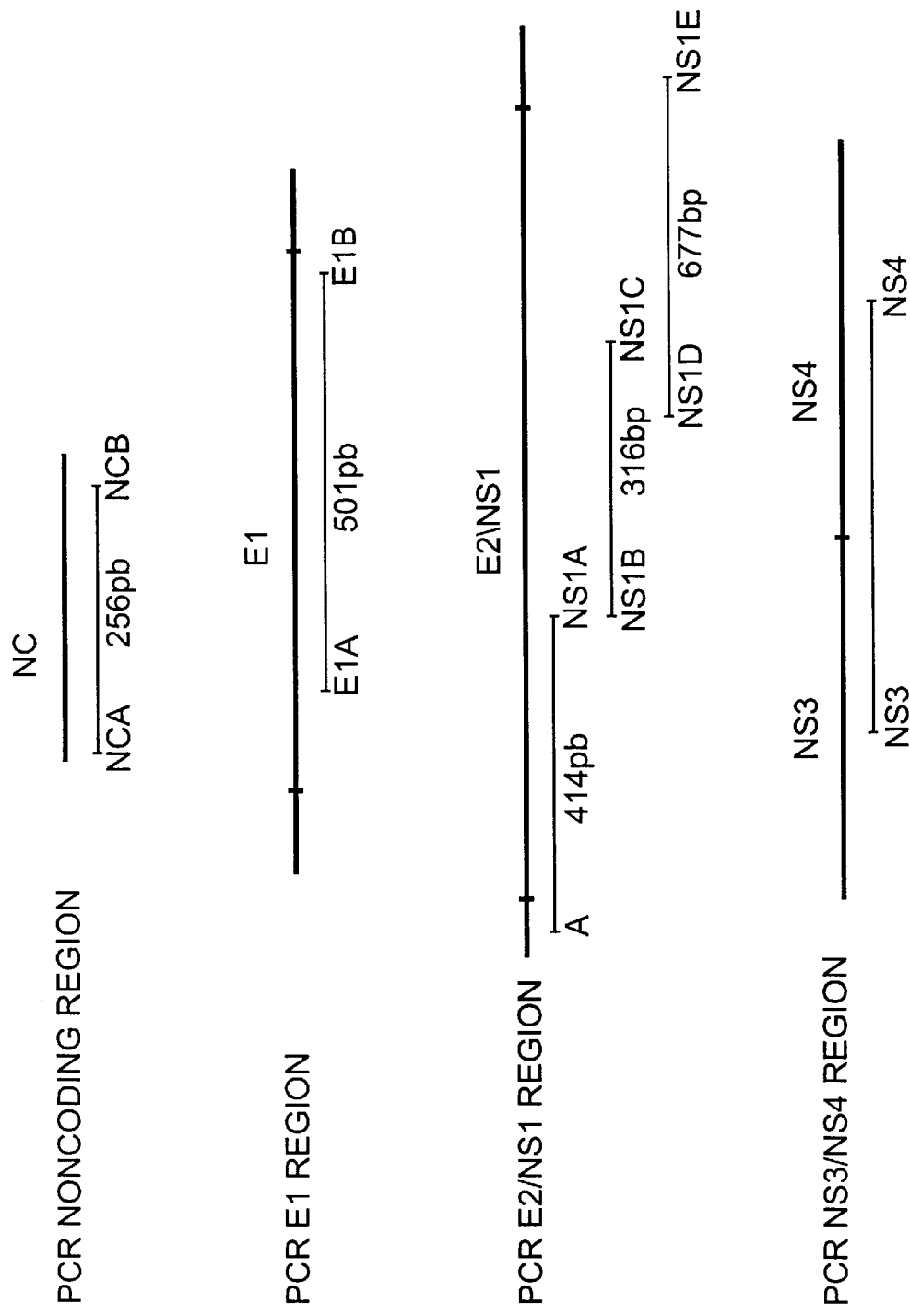

United States Patent [19]

Brechot et al.

[11] Patent Number: 5,879,904
[45] Date of Patent: Mar. 9, 1999

[54] NUCLEOTIDE AND PEPTIDE SEQUENCES OF A HEPATITIS C VIRUS ISOLATE, DIAGNOSTIC AND THERAPEUTIC APPLICATIONS

[75] Inventors: Christian Brechot; Dina Kremsdorf, both of Paris; Colette Porchon, Gentilly, all of France

[73] Assignee: Institut Pasteur, Paris, France

[21] Appl. No.: 965,285

[22] PCT Filed: Jun. 4, 1992

[86] PCT No.: PCT/FR92/00501

§ 371 Date: Mar. 18, 1993

§ 102(e) Date: Mar. 18, 1993

[87] PCT Pub. No.: WO92/21759

PCT Pub. Date: Dec. 10, 1992

[30] Foreign Application Priority Data

Jun. 6, 1991 [FR] France ................................. 91 06882

[51] Int. Cl.⁶ .......................... C07H 21/04; A61K 31/00
[52] U.S. Cl. ........................ 435/69.1; 435/69.3; 435/71.1; 435/235; 435/252.3; 435/320.1; 536/23.1; 536/23.72
[58] Field of Search ....................... 435/5.6, 69.1, 435/71.1, 172.3, 235.1, 240.2, 320.1, 91.1, 69.3, 235, 252.3; 536/23.1, 23.72

[56] References Cited

FOREIGN PATENT DOCUMENTS

| | | |
|---|---|---|
| 0318216 | 5/1989 | European Pat. Off. . |
| 0398 748 | 11/1990 | European Pat. Off. . |
| WO89/04669 | 6/1989 | WIPO . |
| WO90/00597 | 1/1990 | WIPO . |
| WO90/11089 | 10/1990 | WIPO . |

OTHER PUBLICATIONS

Choo et al, Science, vol. 244, 21 Apr. 1989, pp. 359–362, "Kolation of a cDNA Clone Derived from a Blood–Borne Non–A, Non–B Viral Hepatitis Genome".

Weiner et al, Virology, vol. 180, 1991, pp. 842–848, "Variable and Hypervariable Domains are Found in the Regions of HCV Corresponding to the Flavivirus Envelope and NS1 Proteins and the Pesvirus Envelope Glycoproteins".

Norio Ogata et al., Proc. Natl. Acad. Sci. USA, vol. 88, pp. 3392–3396, Apr. 1991, "Nucleotide sequence and mutation rate of the H strain of hepatitis C virus".

Okamoto et al., Japan J. Exp. Med., vol. 60, No. 3, 1990, pp. 167–177.

Weiner et al., Virology, vol. 180, No. 2, Feb. 1991, pp. 842–848.

*Primary Examiner*—Laurie Scheiner
*Attorney, Agent, or Firm*—Finnegan, Henderson, Farabow, Garrett & Dunner, L.L.P.

[57] ABSTRACT

This invention relates to oligonucleotides encoding HCV E1 peptides, labeled oligonucleotide probes, recombinant DNA molecules comprising HCV E1 nucleotides, plasmids, expression vectors, transformed hosts, analytical kits for detecting nucleotide sequences of hepatitis C virus, and process for preparing polypeptides.

8 Claims, 19 Drawing Sheets

```
1  CCATGGCGTTAGTATGAGTGTCGTACAGCCTCCAGGACCCCCTCCCGGAGAGCCATA        60
2  ..............G..........................................        60
3  ..............G..........................................        60
4  ..............G..........................................        60

1  GTGGTCTGCGGAGCCGGTGAGTACACCGGAATTGCCAGGACGACCGGGTCCTTTCTTGGA     120
2  ................A.........................................     120
3  ..........................................................     120
4  ................A.........................................     120

1  TCAACCCGCTCAATGCCTGGAGATTTGGGCGTGCCCCCGCAAGACTGCTAGCCGAGTAGT     180
2  ..A.......................................C..............      180
3  ..A.......................................C.....G........      180
4  ..A.......................................C.....G........      180

1  GTTGGGTCGCGAAAGGCCTTGTGGTACTGCCTGATAGGGTGCTTGCGAGTGCCCCGGGAG     240
2  ............................................................    240
3  ............................................................    240
4  ............................................................    240

1  GTCTCGTAGACCGTGC                                                  256
2  ................                                                  256
3  ................                                                  256
4  ................                                                  256
```

FIG. 2

```
1  TTCTGGAAGACGGCGTGAACTATGCAACAGGGAACCTTCCTGGTTGCTCTTTCTCTATCC    60
2  ..............................................................T    60
3  .............G...........................TT.G..C.............T    60
4  ..............................................................T    60
5  .............G.........................T.TG..C...............T    60

1  TCCTCCTGGCCCTGCTCTCTTGCCTGACTGTGCCCGGTCAGCCTACCAAGTACGCAATT   120
2  .....T..................T...............T.G..........G....   120
3  ...T.....T....G..C..TT....CA.C..A..T..C..T.TG.........G..CG   120
4  ...T......................T.......CA.C..A..T..C..T.TG..........   120
5  ...T....TT....G..C..TT....CA.C..A..T..C..T.TG.........G..CG   120

1  CTCGCGGCGCCTTTACCATGTCACCAATGATTGCCCTAACTCGAGTATTGTGTACGAGACGG   180
2  .CACG..G.......C..................................G........   180
3  TGTC...GA.A.............A..C..T.C.....T...........G........   180
4  .CACA..G....T...........G..C..T.C.....T...........G..A.....   180
5  TGTC...GA.A.............G..C..T.C.....A..C........G..A.....   180

1  CCGATAGCATTCTACACTCTCCCGGGTGTGTCCCTTGCCGTTCGCGAGGGTAACACCTCGA   240
2  ...GC..C..G..A..............C.........T..C..G..........   240
3  .G..CGTG..CA.G..TG.C..C..........C..G..C.....G..AAC..TT....CC   240
4  A...GC..C..G..TA.............C..............C..GT..........   240
5  .G..C.TG..CA.G..TA..........C..........G..........AC....G...CC   240
```

FIG. 3A

```
1  AATGTTGGGTGGCGGTGGCCCCCTACAGTCGCCACCAGAGACGGCAGACTCCCCACAACGC  300
2  ..GG.........A..A......G..G......G..T.A.......G.G..........  300
3  ..GT..C....A...C.CA.T..C..GC...GG...GA.T.C...CG........T...A  300
4  ..GG.........A..A......G..G......G..A..........G.G........  300
5  ..GT..C....A...C.CA.T..C..GC...GG...GA.T.C...CG........T...A  300

1  AGCTTCGACGTCATATCGATCTGCTCGTCGGGAGCGCCACCCTCTGCCCCTCGGCCCTCTATG  360
2  ..................C..........T...............T.............C.  360
3  ..CAT.A.....C..CG....CT.......T....CG..TG.TT......C..TA.G..C.  360
4  ..................C..........T...............T.............C.  360
5  ..CAA.A.....C..CG....CT.......T....GCG..TG.TT......C..TA.G..C.  360

1  TGGGGGACTTGTGCGGGTCCGTCTTCCCGTCGGTCAATTGTTCACCTTCTCCCCCAGGC  420
2  ......C.A........T....T...C...T.T...C...............T.......  420
3  .....TC.C......A.T..T....A.TCC..GC......TA.T......C..G..TC.C  420
4  .....TC........T....T...C...T.T...C...............T.......  420
5  .....TC.C......A.T..T....A.TCC..GC......TA.T......C..G..TC.C  420

1  GCCACTGACAACGCAAGACTGCAACTGTTCCATCTACCCCGGCCACGTAACGGGTCACC  480
2  .........G....................GT.....T..C.T......TA........  480
3  .G..TGA....GTA..G.........G....C..A......T.........TA..C..T..  480
4  .........G....................GT.....T..C.T......TA........  480
5  .G..TGA....GT..G...............C..A......T.........TT..T.A..  480
```

*FIG. 3B*

```
1  GCATGGCATGGGATATGATGA  ........  501
2  .....................  ........  501
3  .......T.............  ........  501
4  .....................  ........  501
5  .......T.............  ........  501
```

FIG. 3C

```
1  LEDGVNYATGNLPGCSFSILLLALLSCLTVPASAYQVRNSRGLYHVTNDCPNSSIV YETA   60
2  ............F.................T......................   .A..   60
3  ............F........I....E...VS.I...................   .A..   60
4  ............F................T......................   .AH    60
5  ............F........I....E...VS.I...................   .A..   60

1  DSI LHSPGCVPCV REGNTSKCWVAVAPTVATRDGRLPT QLRRHIDLLVGSATLCSALYV  120
2  .A..T.........A.R.....MT..............A.......................  120
3  .V.MA.........N.S.R...LT..L.A.NASV....T.....V.......T.AF...M..  120
4  .A..T.........V.R.....MT..............A.......................  120
5  .M.M T.........D.S.R...LT..L.A.NASV....TI....V.......A.AF...M..  120

1  GDLCGSVFLVGQLFTFSPRRHWTTQDCNCSIYPGHVTGHRMAWDMM                  166
2  ..............IS..................G....I.....                  166
3  ...............I...........E.V....G....S.....                  166
4  ...............S..................G....I.....                  166
5  ...................E.V....LS.....                              166
```

FIG. 4

| | | | | |
|---|---|---|---|---|
| 1 | AATGGCTCAACTGCTCTCAGGTCCCGCAAGCCATCTTGGACATGATCGCTGGTGCCCACTG | 60 |
| 2 | .........G..........C..A...A................T.............. | 60 |
| 3 | .........G..........C.CA...A................T.............. | 60 |
| 4 | GG..T.G..GT.........C..A...A.........TG.G.........GG.G.G... | 60 |
| 5 | GG..T.G..GT.A..C..A..C..A...A.........TG.A.........GG.G.G... | 60 |
| 1 | GGGAGTCCTAGCGGGCATAGCGTATTTCTCCATGGTGTGGGGAACTGGGCGAAGGTCCTGCT | 120 |
| 2 | .........G....................................G.......... | 120 |
| 3 | .........G....................................G.......... | 120 |
| 4 | .........G.....C..T..C..C.AT.........A.........T.......A. | 120 |
| 5 | ...........C..T..C..C.AT..................T....TT..A. | 120 |
| 1 | AGTGCTGTTGCTGTTCGCCCGGTCGATGCGGAAACCTACACCACCGGGGAGTACTGC | 180 |
| 2 | ....C...C..A..T.............C.......C..GT.......A..G.C.G | 180 |
| 3 | ............T...............C........AT.GT.T.....ACAAG.C.. | 180 |
| 4 | T...GC.C.A..C..........T...C.G..G.......GT.G......GCGG.CAG | 180 |
| 5 | T..A..C.A..C..T.........T..C.G.C.T...CG.GTG..G......GTGCAA.G | 180 |
| 1 | CAGGACCACGCAAGGACTCGTCAGCTTTCAGTCGAGGCGCCAAGCAGGACATCCAGCT | 240 |
| 2 | .CAC..TGT.TCT...T.T..T.....CC..GCA.C..........A..G....... | 240 |
| 3 | .C.CG...T.TCT...T.T..T.C....CA.C.........T....A........... | 240 |
| 4 | .CAC......CTCCACG...CGTC....C....TCA.CT..G..GTCT...AGA..... | 240 |
| 5 | .CACGT...CTCTAC....ACGTC..C..T..A.CT..G..GTCC...A.A..T..... | 240 |

FIG. 5A

```
1  GATCAACACCAACGGCAGCTGGCACACATTAATCGCACAGCTTTGAACTGTAATGAGAGCCT  300
2  ...............T.................C.....G..CC.......T.......  300
3  ...............T.................C.....G..C........A.......  300
4  TG.G..T..................CA.G..T..CC.A........C.....C....CTC...  300
5  TG.A.....................C....T..C..CA.G..T..CC..........C....CTC...  300

1  CGACACCGGCTGGGCTAGCGCGGGGCTCTTCTATTACCACAAATTCAACTCTTCAGGCTGCCC  360
2  TA.........T.G.A......T........C.....G..............T..  360
3  TA.........T.G.A......TA.......C.A..................G......T..  360
4  .C....T..G.TCC.T..C.C....G....CACA..............G..C..G......  360
5  .C.A..T.G.TCC.T..C.C...G......................................  325

1  CGAGAGGATGGCCAGCTGCAGACCCCTTGCCGATTTCGACCAGGGCTGGGGCCCTATCAG  420
2  T.....C.A.........................C........A......T............  420
3  ..T.............................C...G....A......T..............  420
4  ..G........................C.C...A....A.TGG...C.........A.........C  420
5  ........................................................  325

1  TTATGCCAACGGAACCGGCCCTGAACACCGCCCCTACTGCTGGCACTACCCCCCAAAGCC  480
2  ...............G.........C...C...G..................A...  480
3  ..C..............G.........C...C..A......T..T..................A...  480
4  ...........................................T.T..............  480
5  C...A.TG.GCCTGA.A....G..T.GA.G..T.........T........T..G.G..TCGA..  325
```

FIG.5B

```
1  TTGTGGTATCGTGCCAGCACAGACCGTATGTGGCCAGTGTATTGCTTCACTCCTAGCCC    540
2  ...C...T.....C..GA...GT..G....T.G.A........C......          540
3  ...C.........C...A...G.........G.A........C......            540
4  ..G.........A..C..GTC.CAG..G....T.........C.A....            540
5                                                                325

1  CGTGGTGGTGGGGACGACCAATAAGTTGGGCGCACCCACTTACAACTGGGGTTGTAATGA    600
2  ............A......G.C.G..C......G......C....GAA....        600
3  .T.........................................                 541
4  .T.........................................                 541
5                                                               325

1  TACGGACGTCTTCGTCCTTAATAACACCAGGCCACCGCTGGGCAATTGGTTCGGCTGCAC    660
2  ...........................C..T...............T..T..        660
3  ...........................................                 541
4  ...........................................                 541
5                                                               325

1  CTGGGTGAACTCATCTGGATTTACTAAAGTGTGCGGAGCGCCTCCCTGTGTCATCGGAGG    720
2  ...A.........A......C..C...................T...             720
3  ...........................................                 541
4  ...........................................                 541
5                                                               325
```

*FIG. 5C*

```
1  AGCGGGCAATAACACCTTGTACTGCCCCACTGACTGTTCCGCAAGCATCCGGAAGCTAC   780
2  G..........C......C............T..C.................C..C..   780
3  ..........................................................   541
4  ..........................................................   541
5  ..........................................................   325

1  ATACTCCCGATGTGGCTCCGGTCCTTGGATCACGCCCCAGGTGCCTGGTTGGCTATCCTTA  840
2  ......T..G..C.................C...........A......C.A..C..G..  840
3  ............................................................  541
4  ............................................................  541
5  ............................................................  325

1  TAGGCTCTCTGGCATTATCCCTGTACTGTCAACTACACCCCTGTTCAAGGTCAGGATGTACGT  900
2  ........T...........T.....CA..........A.A..T..AA..............  900
3  ..............................................................  541
4  ..............................................................  541
5  ..............................................................  325

1  GGGAGGGGTCGAGCACAGGCTGCAAGTCGCTTGCAACTGGACGCGGGGCGAGCGTTGTAA  960
2  ........A..........G...CT..C................A........CG.    960
3  ..........................................................  541
4  ..........................................................  541
5  ..........................................................  325
```

*FIG. 5D*

```
1  TCTGGAGGACAGGGGACAGGTCCGAGCTCAGTCCGCTGCTGTCTACCACACAGTGGCA    1020
2  ......A...................................................    1020
3  ..........................C...T.A.....A.C..T.............     541
4  ..........................................................    541
5                                                                325

1  GGTCCCTCCCCGTGTCCTTTACGACCTTGCCAGCCTTGACTACCGGCCTCATCCCACCTCCA  1080
2  ..............................................................  1080
3  ..................C..A...C..A..........T.C.................     541
4  ..............................................................   541
5                                                                   325

1  CCAGAACATCGTGTGGACGTGCAATATTTGTACGGGGTGGGGTCAAGCATTGTGTCCTGGGC  1140
2  ...T..........................................................  1140
3  ...................G..C.......................C.C.............    541
4  ...............................................................   541
5                                                                     325

1  CATCAAGTGGGAGTACGTCATTCTCCCTGTTCTCCCTGCTTGCAGACGCGGCGTCTGCTC    1200
2  ...T.....................................................    1200
3  .........................................C..T...............     541
4  ..........................................................    541
5                                                                 325
```

*FIG. 5E*

```
1  CTGCTTGTGG . . .   1210
2             . . .   1210
3             . . .   541
4             . . .   541
5             . . .   325
```

FIG. 5F

FIG. 6A

```
1  AGNNTLYCPTDCFRKHPEATYSRCGSGPWITPRCLVGYPYRLWHYPCTVNYTLFKVRMYV  300
2  .......H..........D..........................I...I.........  300
3  ............................................................  180
4  ............................................I...I.........  180
5  ............................................................  108

1  GGVEHRLQVACNWTRGERCNLDDRDRSELSPLLLSTTQWVLPCSFTTLPALTTGLIHLH  360
2  .........EA..........D.E..................T................  360
3  ...............................................S..........  180
4  ............................................................  180
5  ............................................................  108

1  QNIVDVQYLYGVGSSIVSWAIKWEYVILLFLLLADARVCSCLW  403
2  ..................A...........V............  180
3  ............................................  180
4  ............................................  180
5  ............................................  108
```

FIG. 6B

```
1   ACAATACGTGTGTCACCCAGAGACAGTCGACTTCAGCCCTTGACCCTACCTTCACCATTGAAA    60
2   ..........................T..................................G.    60
3   GT..C..A...........T...G......T......T.G..T..C....TC.....C..G.    60

1   CAACAACGCTTCCCCAGGATGCTGTCTCCCGCACTCAACGTCGGGGCAGGACTGGCAGGG      120
2   ...TC....C.................................................... 120
3   .G..G..CG.G......A.......G..T.G......G..G..G..A..T...........  120

1   GGAAGCCAGGCATTTACAGATTTGTGGCACCTGGAGAGCGCCCCTCCGGCATGTTCGACT    180
2   .....................C..........................G..G.........    180
3   .C..G..AG......C..T..G........A.T..A......A..G.......G.CG......T.    180

1   CGTCCGTCCCTCTGCGAGTGCTATGACGCAGGCTGTGCTTGGTATGAGCTCACGCCCGCCG    240
2   ......................T.........T........................G..........T.    240
3   ..T..G......A..T......T........G..............................    240

1   AGACCACAGTCAGGCTACGAGCATACATGAACACCCCGGGACTTCCCGTGTGCCAAGACC    300
2   ..................G...............G.........G.....C.........    300
3   .....T..T...T.G..T...C.A..T..A..A..GT.G......C.........    300
```

FIG. 8A

```
1  ATCTTGAGTTTTGGGAGGGCGTCTTCACGGGTCTCACCCATATAGACGCCCACTTCCTAT  360
2  ......A....................T..A..C....T.......T....          360
3  .......G........C.....A.........A..C..................T.G.   360

1  CCCAGAGACAAAGCAGAGTGGGGGAAAAACCTTCCTTACCTGGTAGCGTACCAAGCCACCGTGT  420
2  ........................G...........................          420
3  ......T......GCA..A..C...T.C..C........A...........          420

1  GCGCTAGGGCCCAAGCCCCCCCGTCGTGGGACCAGATGTGGAAGTGCTTGATTCGTC  480
2  ..............T.............A...............T..C...      480
3  .......C......TA.G..T..A..T..A.......T..A.....TC.C..A..G.  480

1  TCAAGCCCCACCCTCCATGGGCCAAACACCCCTGCTATACCGACTGGGCGCTGTTCAGAATG  540
2  .........................................A........          540
3  ..A....T..G..G..C.........G.........G..TA.G..A..A..C..C..     540

1  AAGTCACCCCTGACGCCACCCAATCACCAAATATATCATGACATGCATGTCGGCTGACCCTGG  600
2  ..A.....................G..............C........          600
3  ..G.......C..A.....T..A.......                       569
```

FIG. 8B

```
1  AGGTCGTCACGAGTACCTGGGTGCTCGTGGGCGGCGTTCTGGCTGCTTTGGCCGCGTATT   660
2  ...........C..............T.......C.........................   660
3  ............................................................   569

1  GCCTATCCACAGGCTGCGTGGTCATAGTAGGCAGGGTCATTTTGTCCGGGAAGCCGGCAA   720
2  ...G..A.................G...............G.C................   720
3  ............................................................   569

1  TCATACCCGACACAGGGAAGTCCTCTACCGGGAGTTCGATGAGATGGAAGAGTGCTCTCAGC  780
2  ........T.........................A........................   780
3  ............................................................   569

1  ACTTGCCATACACATCGAGCAAGGGATGATGCTCGCCCGAGCAGTTCAAGCAGAAGGCCCTCG  840
2  ....A..G....................................................   840
3  ............................................................   569

1  GCCTCCTGCAAACACGGTCCCGCCAGCAGAGGTCATCACCCCTGTCCAGACCAACT       900
2  .......G..CGC.............T........G........................   900
3  ............................................................   569

1  GGCAGAGACTCGAGGCCTTCTGGGCGAAGCATATGTGGAACTT                    943
2  ...A.A..........A..........................                    943
3  ............................................................   569
```

*FIG. 8C*

```
1   NTCNVQTVQTVDFSLDPTFTIETTLPQDAVSRTQRRGRTGRGKPGIYRFVAPGERPSGMFDS    60
2   .............I...................RR........T......A........    60
3   .........L........V..................................       60

1   SVLCECYDAGCAWYELTPAETTVRLRAYMNTPGLPVCQDHLEFWEGVFTGLTHIDAHFLS   120
2   ............................................................  120
3   ......................S......L..................S............  120

1   QTKQSGENLPYLVAYQATVCARAQAPPPSWDQMWKCLIRLKPTLHGPTPLLYRLGAVQNE   180
2   ....A.D.F........................K..........................  180
3   ............................................................  180

1   VTLTMPITKYIMTCMSADLEVVTSTWVLVGGVLAALAAYCLSTGCVVIVGRVILSGKPAI   240
2   I....V.......................................V..............  240
3   .................                                             189

1   IPDREVLYREFDEMEECSQHLPYIEQGMMLAEQFKQKALGLLQTRSRQAEVITPAVQTNW   300
2   ..........................................A......A....E...   300
3                                                                  189

1   QRLEAFWAKHMWN                                                 313
2   .K..T........                                                 313
3                                                                 189
```

FIG. 9

NUCLEOTIDE AND PEPTIDE SEQUENCES OF A HEPATITIS C VIRUS ISOLATE, DIAGNOSTIC AND THERAPEUTIC APPLICATIONS

The present invention relates to nucleotide and peptide sequences of a European, more particularly French, strain of the hepatitis C virus, as well as to the diagnostic and therapeutic applications of these sequences.

The hepatitis C virus is a major causative agent of infections by viruses previously called "Non-A Non-B" viruses. Infections by the C virus in fact now represent the most frequent forms of acute hepatitides and chronic Non-A Non-B hepatitides (Alter et al. (1), Choo et al., (3); Hopf et al., (5); Kuo et al., (8); Miyamura et al., (11). Furthermore, there is a relationship (the significance of which is still poorly understood) between the presence of anti-HCV antibodies and the development of primary liver cancers. It has also been shown that the hepatitis C virus is involved in both chronic or acute Non-A Non-B hepatitides linked to transfusions of blood products or of sporadic origin.

The genome of the hepatitis C virus has been cloned and the nucleotide sequence of an American isolate has been described in EP-A-0 318 216, EP-A-0 363 025, EP-A-0 388 232 and WO-A-90/14436. Moreover, data is currently available on the nucleotide sequences of several Japanese isolates relating both to the structural region and the nonstructural region of the virus (Okamoto et al., (12), Enomoto et al., (4), Kato et al., (6); Takeuchi et al., (15 and 16)). The virus exhibits some similarities with the group comprising Flavi- and Pestiviruses; however, it appears to form a distinct class, different from viruses known up until now (Miller and Purcell, (10)).

In spite of the breakthrough which the cloning of HCV represented, several problems persist:

- a substantial genetic variability exists in certain regions of the virus which has made it possible to describe the existence of two groups of viruses,
- diagnosis of the viral infection remains difficult in spite of the possibility of detecting anti-HCV antibodies in the serum of patients. This is due to the existence of false positive results and to a delayed seroconversion following acute infection. Finally there are clearly cases where only the detection of the virus RNA makes it possible to detect the HCV infection while the serology remains negative.

These problems have important implications both with respect to diagnosis and protection against the virus.

The authors of the present invention have carried out the cloning and obtained the partial nucleotide sequence of a French isolate of HCV (called hereinafter HCV E1) from a blood donor who transmitted an active chronic hepatitis to a recipient. Comparison of the nucleotide sequences and the peptide sequences obtained with the respective sequences of the American and Japanese isolates showed that there was

- a high conservation of nucleic acids in the noncoding region of HCV E1,
- a high genetic variability in the structural regions called E1 and E2/NS1,
- a smaller genetic variability in the nonstructural region.

The present invention is based on new nucleotide and polypeptide sequences of the hepatitis C virus which have not been described in the abovementioned state of the art.

The subject of the present invention is thus a DNA sequence of HCV E1 comprising a DNA sequence chosen from the nucleotide sequences of at least 10 nucleotides between the following nucleotides (n); $n_{118}$ to $n_{138}$; $n_{177}$ to $n_{202}$; $n_{233}$ to $n_{247}$; $n_{254}$ to n272 and $n_{272}$ to $n_{288}$ represented in the sequence SEQ ID NO:2, and, $n_{156}$ to $n_{170}$; $n_{170}$ to $n_{217}$; $n_{267}$ to $n_{263}$ and $n_{310}$ to $n_{334}$ represented in the sequence SEQ ID NO:4; as well as analogous nucleotide sequences resulting from degeneracy of the genetic code.

The subject of the invention is in particular the following nucleotide sequences: SEQ ID NO:2, SEQ IS NO:4 and SEQ ID NO:6.

The oligonucleotide sequences may be advantageously synthesised by the Applied Bio System technique.

The subject of the invention is also a peptide sequence of HCV E1 comprising a peptide sequence chosen from the sequences of at least 7 amino acids between the following amino acids (aa): $aa_{58}$ to $aa_{66}$; $aa_{76}$ to $aa_{101}$ represented in the peptide sequence SEQ ID NO:3; $aa_{49}$ to $aa_{78}$; $aa_{98}$ to $aa_{111}$; $aa_{123}$ to $aa_{133}$; $aa_{140}$ to $aa_{149}$ represented in the peptide sequence SEQ ID NO:5; as well as homologous peptide sequences which do not induce modification of biological and immunological properties.

Preferably, the peptide sequence is chosen from the following amino acid sequences: $aa_{58}$ to aa66; $aa_{76}$ to $aa_{101}$, represented in the peptide sequence SEQ ID NO:3; $aa_{49}$ to $aa_{78}$; $aa_{98}$ to $aa_{111}$; $aa_{123}$ to $aa_{133}$ and $aa_{140}$ to $aa_{149}$ represented in the peptide sequence SEQ ID NO:5.

Moreover, the peptide sequence is advantageously chosen from the peptide sequences SEQ ID NO:3, SEQ ID NO:5 and SEQ ID NO:7.

The subject of the invention is also a nucleotide sequence encoding a peptide sequence as defined above.

Moreover, the subject of the invention is a polynucleotide probe comprising a DNA sequence as defined above.

The subject of the invention is also an immunogenic peptide comprising a peptide sequence as defined above.

The peptide sequences according to the invention can be obtained by conventional methods of synthesis or by the application of genetic engineering techniques comprising the insertion of a DNA sequence, encoding a peptide sequence according to the invention, into an expression vector such as a plasmid and the transformation of cells using this expression vector and the culture of these cells.

The subject of the invention is also plasmids or expression vectors comprising a DNA sequence encoding a peptide sequence as defined above as well as hosts transformed using this vector.

The preferred plasmids are those deposited with CNCM on 5 Jun. 1991 under the numbers I-1105, I-1106 and I-1107.

The subject of the invention is also monoclonal antibodies directed against a peptide sequence according to the invention or an immunogenic sequence of such a polypeptide.

The monoclonal antibodies according to the invention can be prepared according to a conventional technique. For this purpose, the polypeptides may be coupled, if necessary, to an immunogenic agent such as tetanus anatoxin using a coupling agent such as glutaraldehyde, a carbodiimide or a bisdiazotised benzidine.

The present invention also encompasses the fragments and the derivatives of monoclonal antibodies according to the invention. These fragments are especially F(ab')$_2$ fragments which can be obtained by enzymatic cleavage of the antibody molecules with pepsin, the Fab' fragments which can be obtained by reducing the disulphide bridges of the F(ab')$_2$ fragments, and the Fab fragments which can be obtained by enzymatic cleavage of the antibody molecules with papain in the presence of a reducing agent. These fragments, as well as the Fc fragments, can also be obtained by genetic engineering.

The derivatives of monoclonal antibodies are for example antibodies or fragments of these antibodies to which markers, such as a radioisotopes, are attached. The derivatives of monoclonal antibodies are also antibodies or fragments of these antibodies to which therapeutically active molecules are attached.

The subject of the invention is also an analytical kit for the detection of nucleotide sequences specific to the HVC E1 strain, comprising one or more probes as defined above.

The subject of the present invention is also an in vitro diagnostic process involving the detection of antigens specific to HCV E1, in a biological sample possibly containing the said antigens, in which, the biological sample is exposed to an antibody or an antibody fragment, as defined above; as well as a diagnostic kit for carrying out the process.

The subject of the invention is also an in vitro diagnostic process involving the detection of antibodies specific to HCV E1 in a biological sample possibly containing the said antibodies, in which a biological sample is exposed to an antigen containing an epitope corresponding to a peptide sequence, as well as a diagnostic kit for the detection of specific antibodies, comprising an antigen containing an epitope corresponding to a peptide sequence as defined above.

These procedures may be based on a radioimmunological method of the RIA, RIPA or IRMA type or an immunoenzymatic method of the WESTERN-BLOT type carried out on strips or of the ELISA type.

The subject of the invention is also a therapeutic composition comprising monoclonal antibodies or fragments of monoclonal antibodies or derivatives of monoclonal antibodies as defined above.

Advantageously, the monoclonal antibody derivatives are monoclonal antibodies or fragments of these antibodies attached to a therapeutically active molecule.

The subject of the invention is also an immunogenic composition containing an immunogenic sequence as defined above, optionally attached to a carrier protein, the said immunogenic sequence being capable of inducing protective antibodies or cytotoxic T lymphocytes. Anatoxins such as tetanus anatoxin may be used as carrier protein. Alternatively, immunogens produced according to the MAP (Multiple Antigenic Peptide) technique may also be used.

In addition to the immunogenic peptide sequence, the immunogenic composition may contain an adjuvant possessing immunostimulant properties.

The following are among the adjuvants which may be used: inorganic salts such as aluminium hydroxide, hydrophobic compounds or surface-active agents such as incomplete Freund's adjuvant, squalene or liposomes, synthetic polynucleotides, microorganisms or microbial components such as murabutide, synthetic artificial molecules such as imuthiol or levamisole, or alternatively cytokines such as interferons α, β, γ or interleukins.

The subject of the invention is also a process for assaying a peptide sequence as defined above, comprising the use of monoclonal antibodies directed against this peptide sequence.

The subject of the invention is also a process for preparing a peptide sequence as defined above, comprising the insertion of a DNA sequence, encoding the peptide sequence, into an expression vector, the transformation of cells using this expression vector and the culture of the cells.

The production of the DNA of the sequences of the HCV E1 strain will be described below in greater detail with reference to the accompanying figures in which:

FIG. 1 represents the location of the amplified and sequenced HCV E1 regions;

FIG. 2 represents the comparison of the nucleotide sequence of HCV E1 (1) [SEQ ID NO:1], in the non-coding region, with the sequences of an American isolate (2) [SEQ ID NO:24] and two Japanese isolates: HCJ1 (3) [SEQ ID NO:25] and HCJ4 (4) [SEQ ID NO:26] respectively described in WO-A-90/14436 and by Okamoto et al. (12);

FIG. 3 represents the comparison of the nucleotide sequence of HCV E1 (1) [SEQ ID NO:3], in the region E1, with the sequences of an American isolate (HCVpt) (2) [SEQ ID NO:27] described in WO 90/14436 and three Japanese isolates: HCVJ-1 (3) [SEQ ID NO:28], HCJ1 (4) [SEQ ID NO:29] and HCJ4 (5) [SEQ ID NO:30] described in Takeuchi et al. (15); Okamoto et al. (12);

FIG. 4 represents the comparison of the aminoacid sequence, in the region E1, of HCV E1 (1) [SEQ ID NO:3] with the American isolate HCVpt (2) [SEQ ID NO:31] and the Japanese isolates: HCVJ1 (3) [SEQ ID NO:32], HCJ1 (4) [SEQ ID NO:33] and HCJ4 (5) [SEQ ID NO:34]; the variable regions are boxed;

FIG. 5 represents the comparison of the nucleotide sequence, in the region E2/NS1, of HCV E1 (1) [SEQ ID NO:4] with the American isolate HCVpt (2) [SEQ ID NO:35] described in WO-A-90/14436 and the Japanese isolates HCJ1 (3) [SEQ ID NO:36], HCJ4 (4) [SEQ ID NO:37] and HCVJ1 (5) [SEQ ID NO:38] described by Okamoto et al. (12); Takeuchi et al. (15);

FIG. 6 represents a comparison of the aminoacid sequence, in the region E2/NS1, of HCV E1 (1) [SEQ ID NO:5] with the American isolate HCVpt (2) [SEQ ID NO:39] and the Japanese isolates HCJ1 (3) [SEQ ID NO:40], HCJ4 (4) [SEQ ID NO:41] and HCVJ1 (5) [SEQ ID NO:42]; the variable regions are boxed;

FIG. 7 represents the hydrophilicity profile of HCV E1 in the region E2/NS1; the hydrophobic regions are located under the middle line;

FIG. 8 represents the comparison of the nucleotide sequence, in the region NS3/NS4, of HCV E1 (1) [SEQ ID NO:6] with the American isolate HCVpt (2) [SEQ ID NO:43] described in WO-A-90/14436 and the Japanese isolate HCVJ1 (3) [SEQ ID NO:44] described by Kubo et al. (7);

FIG. 9 represents the comparison of the aminoacid sequence, in the region NS3/NS4, of HCV E1 (1) [SEQ ID NO:6] with the American isolate HCVpt (2) [SEQ ID NO:45] and the Japanese isolate HCVJ1 (3) [SEQ ID NO:46].

I- Preparation of the Nucleotide Sequences

1) Preparation of the HCV E1 RNA

The HCV E1 RNA was prepared as previously described in EP-A-0,318,216 from the serum of a French blood donor suffering from a chronic hepatitis, anti-HCV positive (anti-C100) (Kubo et al. (7)).

100 μl of serum were diluted in a final volume of 1 ml, in the following extraction buffer: 50 mM tris-HCl, pH.8, 1 mM EDTA, 100 mM NaCl, 1 mg/ml of proteinase K, and 0.5% SDS. After digestion with proteinase K for 1 h at 37° C., the proteins were extracted with one volume of TE-saturated phenol (10 mM Tris-HCl, pH.8, 1 mM EDTA). The aqueous phase was then extracted twice with one volume of phenol/chloroform (1:1) and once with one volume of chloroform. The aqueous phase was then adjusted to a final concentration of 0.2M sodium acetate and the nucleic acids were precipitated by the addition of two volumes of ethanol. After centrifugation, the nucleic acids were suspended in 30 μl of DEPC-treated sterile distilled water.

2) Reverse Transcription and Amplification A complementary DNA (cDNA) was synthesised using as primer either oligonucleotides specific to HCV, represented in Table I below, or a mixture of hexanucleotides not specific to HCV, and murine reverse transcriptase. A PCR (Polymerase Chain Reaction) was carried out over 40 cycles at the following temperatures: 94° C. (1 min), 55° C. (1 min), 72° C. (1 min), on the cDNA thus obtained, using pairs of primers specific to HCV (Table I below). Various HCV primers were made from the sequence of HCV prototype (HCVpt), isolated from a chronically infected chimpanzee (Bradley et al. (2); Alter et al. (1), EP-A-0,318,216). The nucleotide sequence of the 5' region of the E2/NS1 gene was obtained using a strategy derived from the sequence-independent single primer amplification technique (SISPA) described by Reyes et al. (13). It consists in ligating double-stranded adaptors to the ends of the DNA synthesised using an HCV-specific primer localised in 5' of the HCVpt sequence (primer NS1A in Table I). A semi-specific amplification is then carried out using an HCV-specific primer as well as a primer corresponding to the adaptor. This approach makes it possible to obtain amplification products spanning the 5' region of the primer used for the synthesis of the cDNA.

(bp) fragment located in position -259 to -4 in HCVpt as described in WO-A-90/14436. Comparison of the HCV E1 sequence with those previously published shows a very high nucleic acid conservation (FIG. 2).

2) Nucleotide and Peptide Sequences of HCV E1 in the Structural Region

The nucleotide sequences probably correspond to two regions encoding the virus envelope proteins (currently designated as the E1 and E2/NS1 regions).

For the E1 region, the sequence obtained for HCV E1 corresponds to the 3' moiety of the gene. It has been called ID SEQ No.2. This 501-bp sequence is located in position 470 and 973 in the HCVpt sequence as described in WO-A-90/14436. Comparison of this sequence with those previously described shows a high genetic variability (FIG. 3). Indeed, depending on the isolates studied, a difference of 10 to 27% in nucleic acid composition and 7 to 20% in amino acid composition may be observed as shown in Table II below. Furthermore, comparison of the peptide sequence reveals the existence of two hypervariable regions which are boxed in FIG. 4.

For the E2/NS1 region, the HVC E1 sequence data were obtained from three overlapping amplification products (FIG. 1). The consensus sequence thus obtained (1210 bp)

TABLE I

Sequence of the primers and probes.

a) Primers[a]:

| | |
|---|---|
| NS3 | (+) 5' ACAATACGTGTGTCACC (3013–3029) [SEQ ID NO:8] |
| NS4 | (−) 5' AAGTTCCACATATGCTTCGC (3955–3935) [SEQ ID NO:9] |
| NS1A | (−) 5' TCCGTTGGCATAACTGATAG (83–64) [SEQ ID NO:10] |
| NS1B | (+) 5' CTATCAGTTATGCCAACGGA (64–83) [SEQ ID NO:11] |
| NS1C | (−) 5' GTTGCCCGCCCCTCCGATGT (380–361) [SEQ ID NO:12] |
| NS1D | (+) 5' CCCAGCCCCGTGGTGGTGGG (183–202) [SEQ ID NO:13] |
| NS1E | (−) 5' CCACAAGCAGGAGCAGACGC (860–841) [SEQ ID NO:14] |
| NCA | (+) 5' CCATGGCGTTAGTATGAGT (−259—239) [SEQ ID NO:15] |
| NCB | (−) 5' GCAGGTCTACGAGACCTC (−4—23) [SEQ ID NO:16] |
| E1A | (+) 5' TTCTGGAAGACGGCGTGAAC (470–489) [SEQ ID NO:17] |
| E1B | (−) 5' TCATCATATCCCATGCCATG (973–954) [SEQ ID NO:18] | b) probes[a]:

| | |
|---|---|
| NS3/NS4 | (+) 5'CCTTCACCATTGAGACAATCACGCTCCCCCAGGATGCTGT (3058–3097) [SEQ ID NO:19] |
| NS1 | (+) 5'CTGTCCTGAGAGGCTAGCCAGCTGCCGACCCCTTACCGAT (5–44) [SEQ ID NO:20] |
| NS1B/C | (+) 5'AGGTCGGGCGCGCCCACCTACAGCTGGGGTGAAAATGATA (210–248) [SEQ ID NO:21] |
| NC | (+) 5'GTGCAGCCTCCAGGACCCCC (235—216) [SEQ ID NO:22] |
| E1 | (−) 5'CTCGTACACAATACTCGAGT (646–627) [SEQ ID NO:23] |

[a]The nucleotide sequences and their locations correspond to the HCV prototype (HCVpt) (EP-A-0, 318, 216 and WO-A-90/14436).

3) Cloning and Sequencing

The amplification products were cloned into M13 mp19 or into the bacteriophage lambda gt 10 as described by Thiers et al. (17). The probes used for screening the DNA sequences are represented in Table I above. The nucleotide sequence of the inserts was determined by the dideoxynucleotide-based method described by Sanger et al., (14).

II-Study of the Nucleotide Sequences of the French Isolate (HCV E1)

The location of the various amplification products which made it possible to obtain the nucleotide sequence of the HCV E1 isolate in nonstructural and structural regions as well as in the noncoding region of the virus, is schematically represented in FIG. 1.

1) Nucleotide Sequence of HCV E1 in the Noncoding 5' Region

Figure 7:
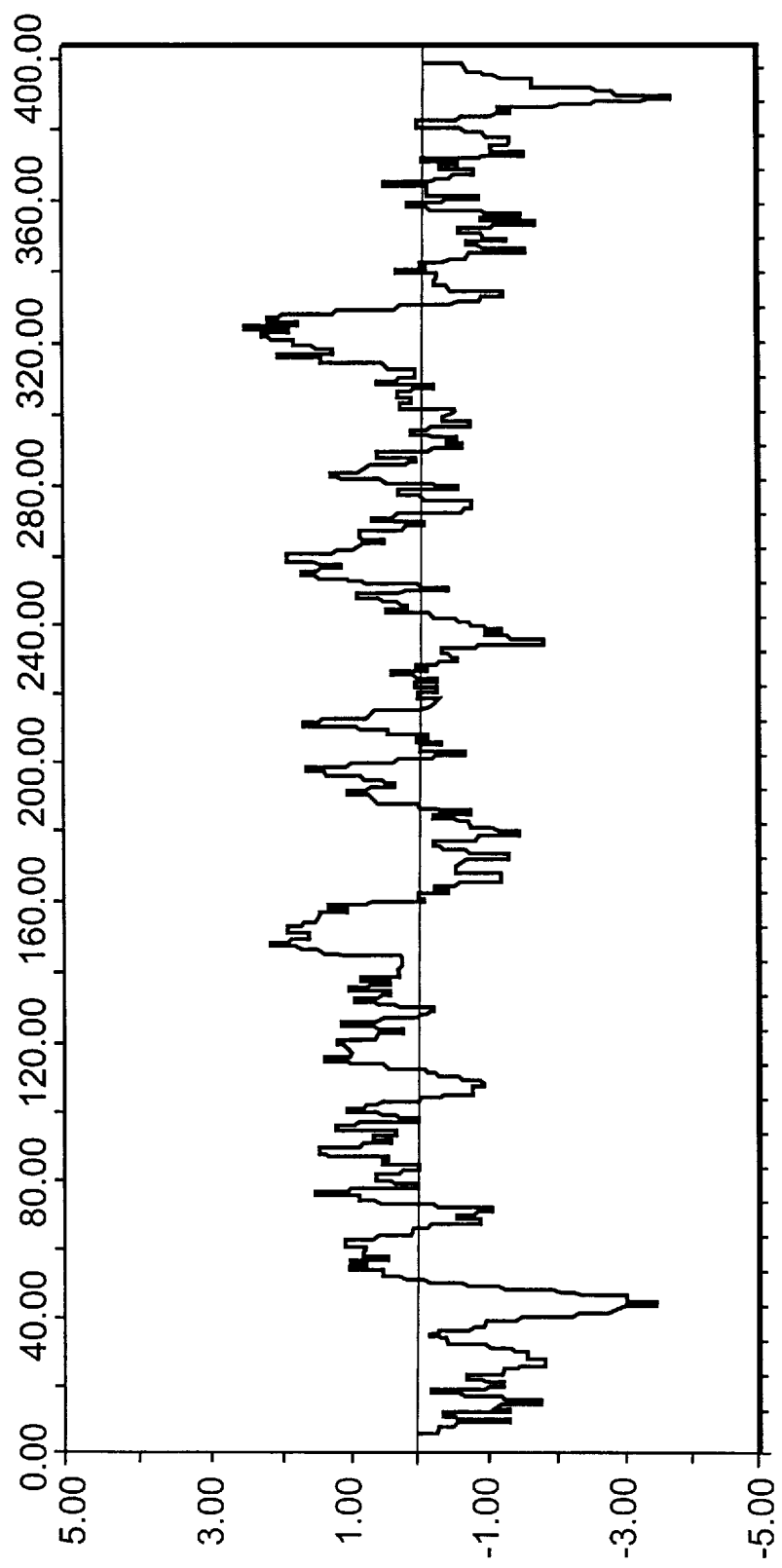

The amplified and sequenced noncoding 5' region of HCV E1 is called ID SEQ No.1. It corresponds to a 256-base pair contains the entire E2/NS1 gene and was called ID SEQ No.3. The sequence of the E2/NS1 region of HCV E1 is situated in position 999 and 2209 compared with the HCVpt sequence described in WO-A-90/14436. Comparison of the HCV E1 sequences with the isolates previously described shows a difference of 13 to 33% in the case of nucleic acids and 11 to 30% in the case of amino acids (FIG. 5 and 6, Table II). The highest variability is observed in 5' of the E2/NS1 gene (FIG. 5). Comparison of amino acids shows the existence of four hypervariable regions which are boxed in FIG. 6. The hydrophilicity profile of the E2/NS1 region (Kyte and Dolittle, (9)) is given in FIG. 7. A hydrophilic region flanked by two hydrophobic regions are observed. Both hydrophobic regions probably correspond to the signal sequence as well as to the transmembrane segment. Finally, the central region has ten potential glycolisation [sic] sites (N-X-T/S), which are conserved in the various isolates (FIG. 6).

3) Nucelotide and Peptide Sequence of HCV E1 in the Nonstructural Region

The sequence data for HCV E1 in the nonstructural region correspond to the 3' and 5' terminal parts of the NS3 and NS4 genes respectively (FIG. 1). The sequence obtained for HCV E1 (943 bp) is located in position 4361 to 5303 in the HCVpt sequence and was called ID SEQ No.4. The sequence homology is 95% with the HCVpt isolate and 78.6% with a Japanese isolate (FIG. 8, Table II above). In the case of the comparison of amino acids, a homology of 98% and 93% was observed with the HCVpt and Japanese isolates respectively (FIG. 8, Table II above).

Thus, comparison of the nucleotide sequence of the HCV E1 isolate with that of the American and Japanese isolates shows that the French isolate is different from the isolates described above. It reveals the existence of highly variable regions in the envelope proteins. The variability of the nonstructural region studied is lower. Finally, the noncoding 5' region shows a high conservation.

These results have implications both for diagnosis and prevention of HVC.

As far as diagnosis is concerned, definition of the hypervariable regions and of the conserved regions can lead to:

the definition of synthetic peptides which allow the expression of epitopes specific to the various HCV groups.

For the envelope protein E1, peptides for the determination of type-specific epitopes are advantageously defined in a region between amino acids 75 to 100 (FIG. 4). Likewise, for the protein E2/NS1, peptides allow [sic] characterisation of specific epitopes are synthesised in regions preferably between amino acids 50 and 149, (FIG. 6).

The expression of all or part of the cloned sequences, in particular clones corresponding to the envelope regions of the virus, make it possible to obtain new antigens for the development of diagnostic reagents and for the production of immunogenic compositions. Finally, the preparation of a substantial part of the nucleotide sequence of this isolate allows the production of the entire length of complementary DNA which can be used for a better understanding of the mechanisms of the viral infection and also for diagnostic and preventive purposes.

TABLE II

Difference in nucleic acids (n.a.) and amino acids (a.a.) between the Frech isolate (HCV E1) and the American (HCVpt) and japanese (HCVJ1, HCJ1, HCJ4) isolates.

| | | HCVpt | HCVJ1 | HCJ1 | HCJ4 |
|---|---|---|---|---|---|
| HCE1 E1 | n.a. | 10.6 | 27.3 | 10.4 | 26.5 |
| | a.a. | 7.2 | 19.9 | 8.4 | 20.5 |
| HCE1 E2/NS1 | n.a. | 12.8 | 33.2% | 14.5% | 29.8% |
| | a.a. | 12.2% | 29.7% | 15.6% | 26.1% |
| HCVE1 NS3/NS4 | n.a. | 5.2% | 21.4% | — | — |
| | a.a. | 2.2% | 6.9% | — | — |

REFERENCES

1. Alter, H. J., Purcell, R. H., Shib, J. W., Melpolder, J. C., Houghton, M., Choo, Q. -L. & Kuo, G. (1989). Detection of antibody to hepatitis C virus in prospectively followed transfusion recipients with acute and chronic Non-A, Non-B hepatitis. New England Journal of Medicine 321, 1494–1500.

2. Bradley, D. W., Cook, E. H., Maynard, J. E., McCaustland, K. A., Ebert, J. W., Dolana, G. H., Petzel, R. A., Kantor, R. J., Heilbrunn, A., Fields, H. A. & Murphy, B. L. (1979). Experimental infection of chimpanzees with antihemophilic (factor VIII) materials: recovery of virus-like particles associated with Non-A, Non-B hepatitis. Journal of Medical Virology 3, 253–269.

3. Choo, Q. -L., Kuo, G., Weiner, A. J., Overby, L. R., Bradley, D. W. & Houghton, M. (1989). Isolation of a cDNA clone derived from a blood-borne Non-A, Non-B viral hepatitis genome. Science 244, 359–362.

4. Enomoto, N., Takada, A., Nakao, T. & Date, T. (1990). There are two major types of hepatitis C virus in Japan. Biochemical and Biophysical Research Communications 170, 1021–1025.

5. Hopf, U., Möller, B., Küther, D., Stemerowicz, R., Lobeck, H., Lüdtke-Handjery, A., Walter, E., Blum, H. E., Roggendorf, M. & Deinhardt, F. (1990). Long-term follow-up of post transfusion and sporadic chronic hepatitis Non-A, Non-B and frequency of circulating antibodies to hepatitis C virus (HCV). Journal of Hepatology 10, 69–76.

6. Kato, N., Hijakata, M., Ootsuyama, Y., Nakagawa, M., Ohkoshi, S., Sugimura, T. & Shimotohno, K. (1990). Molecular cloning of the human hapatitis C virus genome from Japanese patients with Non-A, Non-B hepatitis. Proceedings of the National Academy of Sciences, U.S.A. 87, 9524–9528.

7. Kubo, Y., Takeuchi, K., Boonmar, S., Katayama, T., Choo, Q. -L., Kuo, G., Weiner, A. J., Bradley D. W., Houghton, M., Saito, I. & Miyamura, T. (1989). A cDNA fragment of hepatitis C virus isolated from an implicated donor of post-transfusion Non-A, Non-B hepatitis in Japan. Nucleic Acids Research 17, 10367–10372.

8. Kuo, G., Choo, Q. -L., Alter, H. J., Gitnick, G. L., Redeker, A. G., Purcell, R. H., Miyamura, T., Dienstag, J. L., Alter, M. J., Stevens, C. E., Tegtmeier, G. E., Bonino, F., Colombo, M., Lee, W. S., Kuo, C., Berger, K., Shuster, J. R., Overby, L. R., Bradley, D. W. & Houghton, M. (1989). An assay for circulating antibodies to a major etiologic virus of human Non-A, Non-B hepatitis. Science 244, 362–364.

9. Kyte, W. & Doolittle, R. F. (1982). A simple method for displaying the hydropathic of a protein. Journal of Molecular Biology 157, 105–132.

10. Miller, R. H. & Purcell, R. H. (1990). Hepatitis C virus shares amino acid sequence similarity with pestiviruses and flaviviruses as well as members of two plant virus super groups. Proceedings of the National Academy of Sciences, U.S.A. 87, 2057–2061.

11. Miyamura, T., Saito, T., Katayama, T., Kikuchi, S., Tateda, A., Houghton, M., Choo, Q. -L. & Kuo, G. (1990). Detection of antibody against antigen expressed by molecularly cloned hepatitis C virus cDNA: application to diagnosis and blood screening for posttransfusion hepatitis. Proceedings of the National Academy of Sciences, U.S.A. 87, 983–987.

12. Okamoto, H., Okada, S., Sugiyama, Y., Yotsumoto, S., Tanaka, T., Yoshizawa, H., Tsuda, F., Miyakawa, Y. & Mayumi, M. (1990). The 5' terminal sequence of the hepatitis C virus genome. Japanese Journal of Experimental Medicine 60, 167–177.

13. Reyes, G. R., Purdy, M. A., Kim, J. P., Luk, K. -C., Young, L. M., Fry, K. E. & Bradley, D. W. (1990). Isolation of a cDNA from the virus responsible for enterically transmitted Non-A, Non-B hepatitis. Science 247, 1335–1339.

14. Sanger, F. S., Nicklen, S. & Coulsen, A. R. (1977). DNA sequencing with chain terminating inhibition. Proceedings of the National Academy of Sciences, U.S.A. 74, 5463–5467.

15. Takeuchi, K., Boonmar, S., Kubo, Y., Katayama, T., Harada, H., Ohbayashi, A., Choo, Q., -L., Houghton, M., Saito, I. & Miyamura, T. (1990a). Hepatitis C viral cDNA clones isolated from a healthy carrier donor implicated in post-transfusion Non-A, Non-B hepatitis. Gene 91 (2), 287–291.

16. Takeuchi, K., Kubo, Y., Boonmar, S., Watanabe, Y., Katayama, T., Choo, Q. -L., Kuo, G., Houghton, M., Saito, I. & Miyamura, T. (1990b). Nucleotide sequence of core and envelope genes of the hepatitis C virus genome derived directly from human healthy carriers. Nucleic Acids Research 18, 4626.

17. Thiers, V., Nakajima, E. N., Kremsdorf, D., Mack, D., Schellekens, H., Driss, F., Goude, A., Wands, J., Sninsky, J., Tiollais, P. & Brechot, C. (1988). Transmission of hepatitis B from hepatitis B seronegative subjects. Lancet ii, 1273–1276

| Symbols for the amino acids | | |
|---|---|---|
| A | Ala | alanine |
| C | Cys | cysteine |
| D | Asp | aspartic acid |
| E | Glu | glutamic acid |
| F | Phe | phenylalanine |
| G | Gly | glycine |
| H | His | histidine |
| I | Ile | isoleucine |
| K | Lys | lysine |
| L | Leu | leucine |
| M | Met | methionine |
| N | Asn | asparagine |
| P | Pro | proline |
| Q | Gln | glutamine |
| R | Arg | arginine |
| S | Ser | serine |
| T | Thr | threonine |
| V | Val | valine |
| W | Trp | tryptophan |
| Y | Tyr | tyrosine |

SEQUENCE LISTING ( 1 ) GENERAL INFORMATION:

( i i i ) NUMBER OF SEQUENCES: 46

( 2 ) INFORMATION FOR SEQ ID NO:1:

( i ) SEQUENCE CHARACTERISTICS:
        ( A ) LENGTH: 256 base pairs
        ( B ) TYPE: nucleic acid
        ( C ) STRANDEDNESS: single
        ( D ) TOPOLOGY: linear ( i i ) MOLECULE TYPE: Other
        ( A ) DESCRIPTION: cDNA to genomic RNA ( x i ) SEQUENCE DESCRIPTION: SEQ ID NO:1:

| | | | | | |
|---|---|---|---|---|---|
| CCATGGCGTT | AGTATGAGTG | TCGTACAGCC | TCCAGGACCC | CCCCTCCCGG | GAGAGCCATA | 60 |
| GTGGTCTGCG | GAGCCGGTGA | GTACACCGGA | ATTGCCAGGA | CGACCGGGTC | CTTTCTTGGA | 120 |
| TCAACCCGCT | CAATGCCTGG | AGATTTGGGC | GTGCCCCGC | AAGACTGCTA | GCCGAGTAGT | 180 |
| GTTGGGTCGC | GAAAGGCCTT | GTGGTACTGC | CTGATAGGGT | GCTTGCGAGT | GCCCCGGGAG | 240 |
| GTCTCGTAGA | CCGTGC | | | | | 256 |

( 2 ) INFORMATION FOR SEQ ID NO:2:

( i ) SEQUENCE CHARACTERISTICS:
        ( A ) LENGTH: 501 base pairs
        ( B ) TYPE: nucleic acid
        ( C ) STRANDEDNESS: single
        ( D ) TOPOLOGY: linear ( i i ) MOLECULE TYPE: Other
        ( A ) DESCRIPTION: cDNA to genomic RNA ( x i ) SEQUENCE DESCRIPTION: SEQ ID NO:2:

| | | | | | |
|---|---|---|---|---|---|
| TTCTGGAAGA | CGGCGTGAAC | TATGCAACAG | GGAACCTTCC | TGGTTGCTCT | TTCTCTATCC | 60 |
| TCCTCCTGGC | CCTGCTCTCT | TGCCTGACTG | TGCCCGCGTC | AGCCTACCAA | GTACGCAATT | 120 |
| CTCGCGGCCT | TTACCATGTC | ACCAATGATT | GCCCTAACTC | GAGTATTGTG | TACGAGACGG | 180 |
| CCGATAGCAT | TCTACACTCT | CCGGGGTGTG | TCCCTTGCGT | TCGCGAGGGT | AACACCTCGA | 240 |

| AATGTTGGGT | GGCGGTGGCC | CCTACAGTCG | CCACCAGAGA | CGGCAGACTC | CCCACAACGC | 300 |
| AGCTTCGACG | TCATATCGAT | CTGCTCGTCG | GGAGCGCCAC | CCTCTGCTCG | GCCCTCTATG | 360 |
| TGGGGGACTT | GTGCGGGTCC | GTCTTCCTCG | TCGGTCAATT | GTTCACCTTC | TCCCCCAGGC | 420 |
| GCCACTGGAC | AACGCAAGAC | TGCAACTGTT | CCATCTACCC | CGGCCACGTA | ACGGGTCACC | 480 |
| GCATGGCATG | GGATATGATG | A | | | | 501 |

( 2 ) INFORMATION FOR SEQ ID NO:3:

( i ) SEQUENCE CHARACTERISTICS:
        ( A ) LENGTH: 166 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:3:

```
Leu  Glu  Asp  Gly  Val  Asn  Tyr  Ala  Thr  Gly  Asn  Leu  Pro  Gly  Cys  Ser
 1              5                        10                       15
Phe  Ser  Ile  Leu  Leu  Leu  Ala  Leu  Leu  Ser  Cys  Leu  Thr  Val  Pro  Ala
              20                        25                       30
Ser  Ala  Tyr  Gln  Val  Arg  Asn  Ser  Arg  Gly  Leu  Tyr  His  Val  Thr  Asn
         35                        40                       45
Asp  Cys  Pro  Asn  Ser  Ser  Ile  Val  Tyr  Glu  Thr  Ala  Asp  Ser  Ile  Leu
     50                        55                       60
His  Ser  Pro  Gly  Cys  Val  Pro  Cys  Val  Arg  Glu  Gly  Asn  Thr  Ser  Lys
 65                       70                       75                       80
Cys  Trp  Val  Ala  Val  Ala  Pro  Thr  Val  Ala  Thr  Arg  Asp  Gly  Arg  Leu
                    85                        90                       95
Pro  Thr  Thr  Gln  Leu  Arg  Arg  His  Ile  Asp  Leu  Leu  Val  Gly  Ser  Ala
              100                       105                      110
Thr  Leu  Cys  Ser  Ala  Leu  Tyr  Val  Gly  Asp  Leu  Cys  Gly  Ser  Val  Phe
              115                       120                      125
Leu  Val  Gly  Gln  Leu  Phe  Thr  Phe  Ser  Pro  Arg  Arg  His  Trp  Thr  Thr
              130                       135                      140
Gln  Asp  Cys  Asn  Cys  Ser  Ile  Tyr  Pro  Gly  His  Val  Thr  Gly  His  Arg
145                       150                       155                      160
Met  Ala  Trp  Asp  Met  Met
                    165
```

( 2 ) INFORMATION FOR SEQ ID NO:4:

( i ) SEQUENCE CHARACTERISTICS:
        ( A ) LENGTH: 1210 base pairs
        ( B ) TYPE: nucleic acid
        ( C ) STRANDEDNESS: single
        ( D ) TOPOLOGY: linear ( i i ) MOLECULE TYPE: Other
        ( A ) DESCRIPTION: cDNA to genomic RNA ( x i ) SEQUENCE DESCRIPTION: SEQ ID NO:4:

| AATGGCTCAA | CTGCTCAGGG | TCCCGCAAGC | CATCTTGGAC | ATGATCGCTG | GTGCCCACTG | 60 |
| GGGAGTCCTA | GCGGGCATAG | CGTATTTCTC | CATGGTGGGG | AACTGGGCGA | AGGTCCTGCT | 120 |
| AGTGCTGTTG | CTGTTCGCCG | GCGTCGATGC | GGAAACCTAC | ACCACCGGGG | GGAGTACTGC | 180 |
| CAGGACCACG | CAAGGACTCG | TCAGCCTTTT | CAGTCGAGGC | GCCAAGCAGG | ACATCCAGCT | 240 |
| GATCAACACC | AACGGCAGCT | GGCACATTAA | TCGCACAGCT | TTGAACTGTA | ATGAGAGCCT | 300 |

-continued

```
CGACACCGGC TGGGTAGCGG GGCTCTTCTA TTACCACAAA TTCAACTCTT CAGGCTGCCC        360
CGAGAGGATG GCCAGCTGCA GACCCCTTGC CGATTTCGAC CAGGGCTGGG GCCCTATCAG        420
TTATGCCAAC GGAACCGGCC CTGAACACCG CCCCTACTGC TGGCACTACC CCCCAAAGCC        480
TTGTGGTATC GTGCCAGCAC AGACCGTATG TGGCCCAGTG TATTGCTTCA CTCCTAGCCC        540
CGTGGTGGTG GGGACGACCA ATAAGTTGGG CGCACCCACT TACAACTGGG GTTGTAATGA        600
TACGGACGTC TTCGTCCTTA ATAACACCAG GCCACCGCTG GGCAATTGGT TCGGCTGCAC        660
CTGGGTGAAC TCATCTGGAT TTACTAAAGT GTGCGGAGCG CCTCCCTGTG TCATCGGAGG        720
AGCGGGCAAT AACACCTTGT ACTGCCCCAC TGACTGTTTC CGCAAGCATC CGGAAGCTAC        780
ATACTCCCGA TGTGGCTCCG GTCCTTGGAT CACGCCCAGG TGCCTGGTTG CTATCCTTA        840
TAGGCTCTGG CATTATCCCT GTACTGTCAA CTACACCCTG TTCAAGGTCA GGATGTACGT        900
GGGAGGGGTC GAGCACAGGC TGCAAGTCGC TTGCAACTGG ACGCGGGGCG AGCGTTGTAA        960
TCTGGACGAC AGGGACAGGT CCGAGCTCAG TCCGCTGCTG CTGTCTACCA CACAGTGGCA       1020
GGTCCTCCCG TGTTCCTTTA CGACCTTGCC AGCCTTGACT ACCGGCCTCA TCCACCTCCA       1080
CCAGAACATC GTGGACGTGC AATATTTGTA CGGGGTGGGG TCAAGCATTG TGTCCTGGGC       1140
CATCAAGTGG GAGTACGTCA TTCTCCTGTT TCTCCTGCTT GCAGACGCGC GCGTCTGCTC       1200
CTGCTTGTGG                                                              1210
```

(2) INFORMATION FOR SEQ ID NO:5:

(i) SEQUENCE CHARACTERISTICS:
        (A) LENGTH: 403 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:5:

```
Met Ala Gln Leu Leu Arg Val Pro Gln Ala Ile Leu Asp Met Ile Ala
 1               5                  10                  15
Gly Ala His Trp Gly Val Leu Ala Gly Ile Ala Tyr Phe Ser Met Val
                20                  25                  30
Gly Asn Trp Ala Lys Val Leu Leu Val Leu Leu Leu Phe Ala Gly Val
            35                  40                  45
Asp Ala Glu Thr Tyr Thr Thr Gly Gly Ser Thr Ala Arg Thr Thr Gln
        50                  55                  60
Gly Leu Val Ser Leu Phe Ser Arg Gly Ala Lys Gln Asp Ile Gln Leu
65                  70                  75                  80
Ile Asn Thr Asn Gly Ser Trp His Ile Asn Arg Thr Ala Leu Asn Cys
                85                  90                  95
Asn Glu Ser Leu Asp Thr Gly Trp Val Ala Gly Leu Phe Tyr Tyr His
               100                 105                 110
Lys Phe Asn Ser Ser Gly Cys Pro Glu Arg Met Ala Ser Cys Arg Pro
           115                 120                 125
Leu Ala Asp Phe Asp Gln Gly Trp Gly Pro Ile Ser Tyr Ala Asn Gly
       130                 135                 140
Thr Gly Pro Glu His Arg Pro Tyr Cys Trp His Tyr Pro Pro Lys Pro
145                 150                 155                 160
Cys Gly Ile Val Pro Ala Gln Thr Val Cys Gly Pro Val Tyr Cys Phe
                165                 170                 175
Thr Pro Ser Pro Val Val Val Gly Thr Thr Asn Lys Leu Gly Ala Pro
           180                 185                 190
```

| | | | | | | | | | | | | | | |
|---|---|---|---|---|---|---|---|---|---|---|---|---|---|---|
|Thr|Tyr|Asn 195|Trp|Gly|Cys|Asn|Asp 200|Thr|Asp|Val|Phe 205|Val|Leu|Asn|Asn|
|Thr|Arg 210|Pro|Pro|Leu|Gly|Asn 215|Trp|Phe|Gly|Cys|Thr 220|Trp|Val|Asn|Ser|
|Ser 225|Gly|Phe|Thr|Lys|Val 230|Cys|Gly|Ala|Pro|Cys 235|Val|Ile|Gly|Gly 240| |
|Ala|Gly|Asn|Asn|Thr 245|Leu|Tyr|Cys|Pro|Thr 250|Asp|Cys|Phe|Arg|Lys 255|His|
|Pro|Glu|Ala|Thr 260|Tyr|Ser|Arg|Cys|Gly 265|Ser|Gly|Pro|Trp|Ile 270|Thr|Pro|
|Arg|Cys|Leu 275|Val|Gly|Tyr|Pro|Tyr 280|Arg|Leu|Trp|His|Tyr 285|Pro|Cys|Thr|
|Val|Asn 290|Tyr|Thr|Leu|Phe|Lys 295|Val|Arg|Met|Tyr|Val 300|Gly|Gly|Val|Glu|
|His 305|Arg|Leu|Gln|Val|Ala 310|Cys|Asn|Trp|Thr|Arg 315|Gly|Glu|Arg|Cys|Asn 320|
|Leu|Asp|Asp|Arg|Asp 325|Arg|Ser|Glu|Leu|Ser 330|Pro|Leu|Leu|Leu|Ser 335|Thr|
|Thr|Gln|Trp|Gln 340|Val|Leu|Pro|Cys|Ser 345|Phe|Thr|Thr|Leu|Pro 350|Ala|Leu|
|Thr|Thr|Gly 355|Leu|Ile|His|Leu|His 360|Gln|Asn|Ile|Val|Asp 365|Val|Gln|Tyr|
|Leu|Tyr 370|Gly|Val|Gly|Ser|Ser 375|Ile|Val|Ser|Trp|Ala 380|Ile|Lys|Trp|Glu|
|Tyr 385|Val|Ile|Leu|Leu|Phe 390|Leu|Leu|Leu|Ala|Asp 395|Ala|Arg|Val|Cys|Ser 400|
|Cys|Leu|Trp| | | | | | | | | | | | | |

( 2 ) INFORMATION FOR SEQ ID NO:6:

( i ) SEQUENCE CHARACTERISTICS:
        ( A ) LENGTH: 943 base pairs
        ( B ) TYPE: nucleic acid
        ( C ) STRANDEDNESS: single
        ( D ) TOPOLOGY: linear ( i i ) MOLECULE TYPE: Other
        ( A ) DESCRIPTION: cDNA to genomic RNA ( x i ) SEQUENCE DESCRIPTION: SEQ ID NO:6:

| | | | | | | |
|---|---|---|---|---|---|---|
|ACAATACGTG|TGTCACCCAG|ACAGTCGACT|TCAGCCTTGA|CCCTACCTTC|ACCATTGAAA|60|
|CAACAACGCT|TCCCCAGGAT|GCTGTCTCCC|GCACTCAACG|TCGGGGCAGG|ACTGGCAGGG|120|
|GGAAGCCAGG|CATTTACAGA|TTTGTGGCAC|CTGGAGAGCG|CCCCTCCGGC|ATGTTCGACT|180|
|CGTCCGTCCT|CTGCGAGTGC|TATGACGCAG|GCTGTGCTTG|GTATGAGCTC|ACGCCCGCCG|240|
|AGACCACAGT|CAGGCTACGA|GCATACATGA|ACACCCCGGG|ACTTCCCGTG|TGCCAAGACC|300|
|ATCTTGAGTT|TTGGGAGGGC|GTCTTCACGG|GTCTCACCCA|TATAGACGCC|CACTTCCTAT|360|
|CCCAGACAAA|GCAGAGTGGG|GAAAACCTTC|CTTACCTGGT|AGCGTACCAA|GCCACCGTGT|420|
|GCGCTAGGGC|CCAAGCCCCT|CCCCCGTCGT|GGGACCAGAT|GTGGAAGTGC|TTGATTCGTC|480|
|TCAAGCCCAC|CCTCCATGGG|CCAACACCCC|TGCTATACCG|ACTGGGCGCT|GTTCAGAATG|540|
|AAGTCACCCT|GACGCACCCA|ATCACCAAAT|ATATCATGAC|ATGCATGTCG|GCTGACCTGG|600|
|AGGTCGTCAC|GAGTACCTGG|GTGCTCGTGG|GCGGCGTTCT|GGCTGCTTTG|GCCGCGTATT|660|
|GCCTATCCAC|AGGCTGCGTG|GTCATAGTAG|GCAGGGTCAT|TTTGTCCGGG|AAGCCGGCAA|720|

```
TCATACCCGA CAGGGAAGTC CTCTACCGGG AGTTCGATGA GATGGAAGAG TGCTCTCAGC      780

ACTTGCCATA CATCGAGCAA GGGATGATGC TCGCCGAGCA GTTCAAGCAG AAGGCCCTCG      840

GCCTCCTGCA AACACGGTCC CGCCAGGCAG AGGTCATCAC CCCTGCTGTC CAGACCAACT      900

GGCAGAGACT CGAGGCCTTC TGGGCGAAGC ATATGTGGAA CTT                        943
```

(2) INFORMATION FOR SEQ ID NO:7:

(i) SEQUENCE CHARACTERISTICS:
        (A) LENGTH: 313 amino acids
        (B) TYPE: amino acid
        (D) TOPOLOGY: linear (ii) MOLECULE TYPE: peptide (xi) SEQUENCE DESCRIPTION: SEQ ID NO:7:

```
Asn Thr Cys Val Thr Gln Thr Val Asp Phe Ser Leu Asp Pro Thr Phe
 1               5                  10                  15

Thr Ile Glu Thr Thr Leu Pro Gln Asp Ala Val Ser Arg Thr Gln
                20                  25                  30

Arg Arg Gly Arg Thr Gly Arg Gly Lys Pro Gly Ile Tyr Arg Phe Val
                35                  40                  45

Ala Pro Gly Glu Arg Pro Ser Gly Met Phe Asp Ser Ser Val Leu Cys
            50                  55                  60

Glu Cys Tyr Asp Ala Gly Cys Ala Trp Tyr Glu Leu Thr Pro Ala Glu
65                  70                  75                  80

Thr Thr Val Arg Leu Arg Ala Tyr Met Asn Thr Pro Gly Leu Pro Val
                85                  90                  95

Cys Gln Asp His Leu Glu Phe Trp Glu Gly Val Phe Thr Gly Leu Thr
                100                 105                 110

His Ile Asp Ala His Phe Leu Ser Gln Thr Lys Gln Ser Gly Glu Asn
            115                 120                 125

Leu Pro Tyr Leu Val Ala Tyr Gln Ala Thr Val Cys Ala Arg Ala Gln
            130                 135                 140

Ala Pro Pro Pro Ser Trp Asp Gln Met Trp Lys Cys Leu Ile Arg Leu
145                 150                 155                 160

Lys Pro Thr Leu His Gly Pro Thr Pro Leu Leu Tyr Arg Leu Gly Ala
                165                 170                 175

Val Gln Asn Glu Val Thr Leu Thr His Pro Ile Thr Lys Tyr Ile Met
            180                 185                 190

Thr Cys Met Ser Ala Asp Leu Glu Val Val Thr Ser Thr Trp Val Leu
            195                 200                 205

Val Gly Gly Val Leu Ala Ala Leu Ala Ala Tyr Cys Leu Ser Thr Gly
            210                 215                 220

Cys Val Val Ile Val Gly Arg Val Ile Leu Ser Gly Lys Pro Ala Ile
225                 230                 235                 240

Ile Pro Asp Arg Glu Val Leu Tyr Arg Glu Phe Asp Glu Met Glu Glu
                245                 250                 255

Cys Ser Gln His Leu Pro Tyr Ile Glu Gln Gly Met Met Leu Ala Glu
            260                 265                 270

Gln Phe Lys Gln Lys Ala Leu Gly Leu Leu Gln Thr Arg Ser Arg Gln
            275                 280                 285

Ala Glu Val Ile Thr Pro Ala Val Gln Thr Asn Trp Gln Arg Leu Glu
        290                 295                 300

Ala Phe Trp Ala Lys His Met Trp Asn
305                 310
```

( 2 ) INFORMATION FOR SEQ ID NO:8:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: Other
        ( A ) DESCRIPTION: DNA primer ( x i ) SEQUENCE DESCRIPTION: SEQ ID NO:8:

ACAATACGTG TGTCACC         17

( 2 ) INFORMATION FOR SEQ ID NO:9:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: Other
        ( A ) DESCRIPTION: DNA primer ( x i ) SEQUENCE DESCRIPTION: SEQ ID NO:9:

AAGTTCCACA TATGCTTCGC         20

( 2 ) INFORMATION FOR SEQ ID NO:10:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: Other
        ( A ) DESCRIPTION: DNA primer ( x i ) SEQUENCE DESCRIPTION: SEQ ID NO:10:

TCCGTTGGCA TAACTGATAG         20

( 2 ) INFORMATION FOR SEQ ID NO:11:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: Other
        ( A ) DESCRIPTION: DNA primer ( x i ) SEQUENCE DESCRIPTION: SEQ ID NO:11:

CTATCAGTTA TGCCAACGGA         20

( 2 ) INFORMATION FOR SEQ ID NO:12:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: Other
        ( A ) DESCRIPTION: DNA primer ( x i ) SEQUENCE DESCRIPTION: SEQ ID NO:12:

GTTGCCCGCC CCTCCGATGT         20

(2) INFORMATION FOR SEQ ID NO:13:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: Other
        (A) DESCRIPTION: DNA primer (xi) SEQUENCE DESCRIPTION: SEQ ID NO:13:

```
CCCAGCCCCG TGGTGGTGGG                                         20
```

(2) INFORMATION FOR SEQ ID NO:14:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: Other
        (A) DESCRIPTION: DNA primer (xi) SEQUENCE DESCRIPTION: SEQ ID NO:14:

```
CCACAAGCAG GAGCAGACGC                                         20
```

(2) INFORMATION FOR SEQ ID NO:15:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: Other
        (A) DESCRIPTION: DNA primer (xi) SEQUENCE DESCRIPTION: SEQ ID NO:15:

```
CCATGGCGTT AGTATGAGT                                          19
```

(2) INFORMATION FOR SEQ ID NO:16:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: Other
        (A) DESCRIPTION: DNA primer (xi) SEQUENCE DESCRIPTION: SEQ ID NO:16:

```
GCAGGTCTAC GAGACCTC                                           18
```

(2) INFORMATION FOR SEQ ID NO:17:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: Other
        (A) DESCRIPTION: DNA primer (xi) SEQUENCE DESCRIPTION: SEQ ID NO:17:

```
TTCTGGAAGA CGGCGTGAAC                                         20
```

( 2 ) INFORMATION FOR SEQ ID NO:18:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: Other
        ( A ) DESCRIPTION: DNA primer ( x i ) SEQUENCE DESCRIPTION: SEQ ID NO:18:

TCATCATATC CCATGCCATG        20

( 2 ) INFORMATION FOR SEQ ID NO:19:

( i ) SEQUENCE CHARACTERISTICS:
        ( A ) LENGTH: 40 base pairs
        ( B ) TYPE: nucleic acid
        ( C ) STRANDEDNESS: single
        ( D ) TOPOLOGY: linear ( i i ) MOLECULE TYPE: Other
        ( A ) DESCRIPTION: DNA probe ( x i ) SEQUENCE DESCRIPTION: SEQ ID NO:19:

CCTTCACCAT TGAGACAATC ACGCTCCCCC AGGATGCTGT        40

( 2 ) INFORMATION FOR SEQ ID NO:20:

( i ) SEQUENCE CHARACTERISTICS:
        ( A ) LENGTH: 40 base pairs
        ( B ) TYPE: nucleic acid
        ( C ) STRANDEDNESS: single
        ( D ) TOPOLOGY: linear ( i i ) MOLECULE TYPE: Other
        ( A ) DESCRIPTION: DNA probe ( x i ) SEQUENCE DESCRIPTION: SEQ ID NO:20:

CTGTCCTGAG AGGCTAGCCA GCTGCCGACC CCTTACCGAT        40

( 2 ) INFORMATION FOR SEQ ID NO:21:

( i ) SEQUENCE CHARACTERISTICS:
        ( A ) LENGTH: 40 base pairs
        ( B ) TYPE: nucleic acid
        ( C ) STRANDEDNESS: single
        ( D ) TOPOLOGY: linear ( i i ) MOLECULE TYPE: Other
        ( A ) DESCRIPTION: DNA probe ( x i ) SEQUENCE DESCRIPTION: SEQ ID NO:21:

AGGTCGGGCG CGCCCACCTA CAGCTGGGGT GAAAATGATA        40

( 2 ) INFORMATION FOR SEQ ID NO:22:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: Other
        ( A ) DESCRIPTION: DNA probe ( x i ) SEQUENCE DESCRIPTION: SEQ ID NO:22:

GTGCAGCCTC CAGGACCCCC        20

( 2 ) INFORMATION FOR SEQ ID NO:23:

( i ) SEQUENCE CHARACTERISTICS:
  ( A ) LENGTH: 20 base pairs
  ( B ) TYPE: nucleic acid
  ( C ) STRANDEDNESS: single
  ( D ) TOPOLOGY: linear ( i i ) MOLECULE TYPE: Other
  ( A ) DESCRIPTION: DNA probe ( x i ) SEQUENCE DESCRIPTION: SEQ ID NO:23:

| | | |
|---|---|---|
| CTCGTACACA ATACTCGAGT | | 20 |

( 2 ) INFORMATION FOR SEQ ID NO:24:

( i ) SEQUENCE CHARACTERISTICS:
  ( A ) LENGTH: 256 base pairs
  ( B ) TYPE: nucleic acid
  ( C ) STRANDEDNESS: single
  ( D ) TOPOLOGY: linear ( i i ) MOLECULE TYPE: Other
  ( A ) DESCRIPTION: cDNA to genomic RNA ( x i ) SEQUENCE DESCRIPTION: SEQ ID NO:24:

| | |
|---|---|
| CCATGGCGTT AGTATGAGTG TCGTGCAGCC TCCAGGACCC CCCCTCCCGG GAGAGCCATA | 60 |
| GTGGTCTGCG GAACCGGTGA GTACACCGGA ATTGCCAGGA CGACCGGGTC CTTTCTTGGA | 120 |
| TAAACCCGCT CAATGCCTGG AGATTTGGGC GCGCCCCGC GAGACTGCTA GCCGAGTAGT | 180 |
| GTTGGGTCGC GAAAGGCCTT GTGGTACTGC CTGATAGGGT GCTTGCGAGT GCCCCGGGAG | 240 |
| GTCTCGTAGA CCGTGC | 256 |

( 2 ) INFORMATION FOR SEQ ID NO:25:

( i ) SEQUENCE CHARACTERISTICS:
  ( A ) LENGTH: 256 base pairs
  ( B ) TYPE: nucleic acid
  ( C ) STRANDEDNESS: single
  ( D ) TOPOLOGY: linear ( i i ) MOLECULE TYPE: Other
  ( A ) DESCRIPTION: cDNA to genomic RNA ( x i ) SEQUENCE DESCRIPTION: SEQ ID NO:25:

| | |
|---|---|
| CCATGGCGTT AGTATGAGTG TCGTGCAGCC TCCAGGACCC CCCCTCCCGG GAGAGCCATA | 60 |
| GTGGTCTGCG GAGCCGGTGA GTACACCGGA ATTGCCAGGA CGACCGGGTC CTTTCTTGGA | 120 |
| TAAACCCGCT CAATGCCTGG AGATTTGGGC GCGCCCCGC AAGACTGCTA GCCGAGTAGT | 180 |
| GTTGGGTCGC GAAAGGCCTT GTGGTACTGC CTGATAGGGT GCTTGCGAGT GCCCCGGGAG | 240 |
| GTCTCGTAGA CCGTGC | 256 |

( 2 ) INFORMATION FOR SEQ ID NO:26:

( i ) SEQUENCE CHARACTERISTICS:
  ( A ) LENGTH: 256 base pairs
  ( B ) TYPE: nucleic acid
  ( C ) STRANDEDNESS: single
  ( D ) TOPOLOGY: linear ( i i ) MOLECULE TYPE: Other
  ( A ) DESCRIPTION: cDNA to genomic RNA ( x i ) SEQUENCE DESCRIPTION: SEQ ID NO:26:

| | |
|---|---|
| CCATGGCGTT AGTATGAGTG TCGTGCAGCC TCCAGGACCC CCCCTCCCGG GAGAGCCATA | 60 |

| | | | | | |
|---|---|---|---|---|---|
| GTGGTCTGCG | GAACCGGTGA | GTACACCGGA | ATTGCCAGGA | CGACCGGGTC | CTTTCTTGGA | 120
| TAAACCCGCT | CAATGCCTGG | AGATTTGGGC | GCGCCCCGC | GAGACTGCTA | GCCGAGTAGT | 180
| GTTGGGTCGC | GAAAGGCCTT | GTGGTACTGC | CTGATAGGGT | GCTTGCGAGT | GCCCCGGGAG | 240
| GTCTCGTAGA | CCGTGC | | | | | 256

( 2 ) INFORMATION FOR SEQ ID NO:27:

( i ) SEQUENCE CHARACTERISTICS:
        ( A ) LENGTH: 501 base pairs
        ( B ) TYPE: nucleic acid
        ( C ) STRANDEDNESS: single
        ( D ) TOPOLOGY: linear ( i i ) MOLECULE TYPE: Other
        ( A ) DESCRIPTION: cDNA to genomic RNA ( x i ) SEQUENCE DESCRIPTION: SEQ ID NO:27:

| | | | | | |
|---|---|---|---|---|---|
| TTCTGGAAGA | CGGCGTGAAC | TATGCAACAG | GGAACCTTCC | TGGTTGCTCT | TTCTCTATCT | 60
| TCCTTCTGGC | CCTGCTCTCT | TGCTTGACTG | TGCCCGCTTC | GGCCTACCAA | GTGCGCAATT | 120
| CCACGGGGCT | TTACCACGTC | ACCAATGATT | GCCCTAACTC | GAGTATTGTG | TACGAGGCGG | 180
| CCGATGCCAT | CCTGCACACT | CCGGGGTGCG | TCCCTTGCGT | TCGTGAGGGC | AACGCCTCGA | 240
| GGTGTTGGGT | GGCGATGACC | CCTACGGTGG | CCACCAGGGA | TGGAAGACTC | CCCGCGACGC | 300
| AGCTTCGACG | TCACATCGAT | CTGCTTGTCG | GGAGCGCCAC | CCTCTGTTCG | GCCCTCTACG | 360
| TGGGGACCT | ATGCGGGTCT | GTCTTTCTTG | TCGGCCAATT | GTTCACCTTC | TCTCCCAGGC | 420
| GCCACTGGAC | GACGCAAGGT | TGCAATTGCT | CTATCTATCC | CGGCCATATA | ACGGGTCACC | 480
| GCATGGCATG | GGATATGATG | A | | | | 501

( 2 ) INFORMATION FOR SEQ ID NO:28:

( i ) SEQUENCE CHARACTERISTICS:
        ( A ) LENGTH: 501 base pairs
        ( B ) TYPE: nucleic acid
        ( C ) STRANDEDNESS: single
        ( D ) TOPOLOGY: linear ( i i ) MOLECULE TYPE: Other
        ( A ) DESCRIPTION: cDNA to genomic RNA ( x i ) SEQUENCE DESCRIPTION: SEQ ID NO:28:

| | | | | | |
|---|---|---|---|---|---|
| TTCTGGAGGA | CGGCGTGAAC | TATGCAACAG | GGAATTTGCC | CGGTTGCTCT | TTCTCTATCT | 60
| TCCTCTTGGC | TCTGCTGTCC | TGTTTGACCA | TCCCAGCTTC | CGCTTATGAA | GTGCGCAACG | 120
| TGTCCGGGAT | ATACCATGTC | ACAAACGACT | GCTCCAACTC | AAGCATTGTG | TATGAGGCGG | 180
| CGGACGTGAT | CATGCATGCC | CCCGGGTGCG | TGCCCTGCGT | TCGGGAGAAC | AATTCCTCCC | 240
| GTTGCTGGGT | AGCGCTCACT | CCCACGCTCG | CGGCCAGGAA | TGCCAGCGTC | CCCACTACGA | 300
| CATTACGACG | CCACGTCGAC | TTGCTCGTTG | GGACGGCTGC | TTTCTGCTCC | GCTATGTACG | 360
| TGGGGATCT | CTGCGGATCT | GTTTTCCTCA | TCTCCCAGCT | GTTCACCTTC | TCGCCTCGCC | 420
| GGCATGAGAC | AGTACAGGAC | TGCAACTGCT | CAATCTATCC | CGGCCACGTA | TCAGGCCATC | 480
| GCATGGCTTG | GGATATGATG | A | | | | 501

( 2 ) INFORMATION FOR SEQ ID NO:29:

( i ) SEQUENCE CHARACTERISTICS:
        ( A ) LENGTH: 501 base pairs
        ( B ) TYPE: nucleic acid
        ( C ) STRANDEDNESS: single
        ( D ) TOPOLOGY: linear (i i) MOLECULE TYPE: Other
    (A) DESCRIPTION: cDNA to genomic RNA (x i) SEQUENCE DESCRIPTION: SEQ ID NO:29:

| | | | | | | |
|---|---|---|---|---|---|---|
| TTCTGGAAGA | CGGCGTGAAC | TATGCAACAG | GGAACCTTCC | TGGTTGCTCT | TTCTCTATCT | 60 |
| TCCTTCTGGC | CCTGCTCTCT | TGCCTGACTG | TGCCCGCTTC | AGCCTACCAA | GTGCGCAACT | 120 |
| CCACAGGGCT | TTATCATGTC | ACCAATGATT | GCCCTAACTC | GAGTATTGTG | TACGAGGCGC | 180 |
| ACGATGCCAT | CCTGCATACT | CCGGGGTGTG | TCCCTTGCGT | TCGCGAGGGC | AACGTCTCGA | 240 |
| GGTGTTGGGT | GGCGATGACC | CCCACGGTAG | CCACCAGGGA | CGGAAGACTC | CCCGCGACGC | 300 |
| AGCTTCGACG | TCACATCGAT | CTGCTTGTCG | GGAGCGCCAC | CCTCTGTTCG | GCCCTCTACG | 360 |
| TGGGGGATCT | GTGCGGGTCC | GTCTTCCTTA | TTGGTCAACT | GTTTACCTTC | TCTCCCAGGC | 420 |
| GCCACTGGAC | AACGCAAGGC | TGCAATTGTT | CTATCTACCC | CGGCCATATA | ACGGGTCATC | 480 |
| GCATGGCATG | GGATATGATG | A | | | | 501 |

(2) INFORMATION FOR SEQ ID NO:30:

(i) SEQUENCE CHARACTERISTICS:
    (A) LENGTH: 501 base pairs
    (B) TYPE: nucleic acid
    (C) STRANDEDNESS: single
    (D) TOPOLOGY: linear (i i) MOLECULE TYPE: Other
    (A) DESCRIPTION: cDNA to genomic RNA (x i) SEQUENCE DESCRIPTION: SEQ ID NO:30:

| | | | | | | |
|---|---|---|---|---|---|---|
| TTCTGGAGGA | CGGCGTGAAC | TATGCAACAG | GGAACTTGCC | CGGTTGCTCT | TTCTCTATCT | 60 |
| TCCTCTTGGC | TTTGCTGTCC | TGTTTGACCA | TCCCAGCTTC | CGCTTATGAA | GTGCGCAACG | 120 |
| TGTCCGGGAT | ATACCATGTC | ACGAACGACT | GCTCCAACTC | AAGCATTGTG | TATGAGGCAG | 180 |
| CGGACATGAT | CATGCATACT | CCCGGGTGCG | TGCCCTGCGT | TCGGGAGGAC | AACAGCTCCC | 240 |
| GTTGCTGGGT | AGCGCTCACT | CCCACGCTCG | CGGCCAGGAA | TGCCAGCGTC | CCCACTACGA | 300 |
| CAATACGACG | CCACGTCGAC | TTGCTCGTTG | GGGCGGCTGC | TTTCTGCTCC | GCTATGTACG | 360 |
| TGGGGGATCT | CTGCGGATCT | GTTTTCCTCG | TCTCCCAGCT | GTTCACCTTC | TCGCCTCGCC | 420 |
| GGCATGAGAC | AGTGCAGGAC | TGCAACTGCT | CAATCTATCC | CGGCCATTTA | TCAGGTCACC | 480 |
| GCATGGCTTG | GGATATGATG | A | | | | 501 |

(2) INFORMATION FOR SEQ ID NO:31:

(i) SEQUENCE CHARACTERISTICS:
    (A) LENGTH: 166 amino acids
    (B) TYPE: amino acid
    (D) TOPOLOGY: linear (i i) MOLECULE TYPE: peptide (x i) SEQUENCE DESCRIPTION: SEQ ID NO:31:

| Leu | Glu | Asp | Gly | Val | Asn | Tyr | Ala | Thr | Gly | Asn | Leu | Pro | Gly | Cys | Ser |
|---|---|---|---|---|---|---|---|---|---|---|---|---|---|---|---|
| 1 | | | | 5 | | | | | 10 | | | | | 15 | |
| Phe | Ser | Ile | Phe | Leu | Leu | Ala | Leu | Leu | Ser | Cys | Leu | Thr | Val | Pro | Ala |
| | | | 20 | | | | | 25 | | | | | 30 | | |
| Ser | Ala | Tyr | Gln | Val | Arg | Asn | Ser | Thr | Gly | Leu | Tyr | His | Val | Thr | Asn |
| | | | 35 | | | | | 40 | | | | | 45 | | |
| Asp | Cys | Pro | Asn | Ser | Ser | Ile | Val | Tyr | Glu | Ala | Ala | Asp | Ala | Ile | Leu |
| | | | 50 | | | | | 55 | | | | | 60 | | |

| His | Thr | Pro | Gly | Cys | Val | Pro | Cys | Val | Arg | Glu | Gly | Asn | Ala | Ser | Arg |
| --- | --- | --- | --- | --- | --- | --- | --- | --- | --- | --- | --- | --- | --- | --- | --- |
| 65 | | | | | 70 | | | | | 75 | | | | | 80 |

| Cys | Trp | Val | Ala | Met | Thr | Pro | Thr | Val | Ala | Thr | Arg | Asp | Gly | Arg | Leu |
| --- | --- | --- | --- | --- | --- | --- | --- | --- | --- | --- | --- | --- | --- | --- | --- |
| | | | | 85 | | | | | 90 | | | | | 95 | |

| Pro | Ala | Thr | Gln | Leu | Arg | Arg | His | Ile | Asp | Leu | Leu | Val | Gly | Ser | Ala |
| --- | --- | --- | --- | --- | --- | --- | --- | --- | --- | --- | --- | --- | --- | --- | --- |
| | | | 100 | | | | | 105 | | | | | 110 | | |

| Thr | Leu | Cys | Ser | Ala | Leu | Tyr | Val | Gly | Asp | Leu | Cys | Gly | Ser | Val | Phe |
| --- | --- | --- | --- | --- | --- | --- | --- | --- | --- | --- | --- | --- | --- | --- | --- |
| | | 115 | | | | | 120 | | | | | 125 | | | |

| Leu | Val | Gly | Gln | Leu | Phe | Thr | Phe | Ser | Pro | Arg | Arg | His | Trp | Thr | Thr |
| --- | --- | --- | --- | --- | --- | --- | --- | --- | --- | --- | --- | --- | --- | --- | --- |
| | 130 | | | | | 135 | | | | | 140 | | | | |

| Gln | Gly | Cys | Asn | Cys | Ser | Ile | Tyr | Pro | Gly | His | Ile | Thr | Gly | His | Arg |
| --- | --- | --- | --- | --- | --- | --- | --- | --- | --- | --- | --- | --- | --- | --- | --- |
| 145 | | | | | 150 | | | | | 155 | | | | | 160 |

| Met | Ala | Trp | Asp | Met | Met |
| --- | --- | --- | --- | --- | --- |
| | | | | 165 | |

( 2 ) INFORMATION FOR SEQ ID NO:32:

( i ) SEQUENCE CHARACTERISTICS:
        ( A ) LENGTH: 166 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:32:

| Leu | Glu | Asp | Gly | Val | Asn | Tyr | Ala | Thr | Gly | Asn | Leu | Pro | Gly | Cys | Ser |
| --- | --- | --- | --- | --- | --- | --- | --- | --- | --- | --- | --- | --- | --- | --- | --- |
| 1 | | | | 5 | | | | | 10 | | | | | 15 | |

| Phe | Ser | Ile | Phe | Leu | Leu | Ala | Leu | Leu | Ser | Cys | Leu | Thr | Ile | Pro | Ala |
| --- | --- | --- | --- | --- | --- | --- | --- | --- | --- | --- | --- | --- | --- | --- | --- |
| | | | 20 | | | | | 25 | | | | | 30 | | |

| Ser | Ala | Tyr | Glu | Val | Arg | Asn | Val | Ser | Gly | Ile | Tyr | His | Val | Thr | Asn |
| --- | --- | --- | --- | --- | --- | --- | --- | --- | --- | --- | --- | --- | --- | --- | --- |
| | | | 35 | | | | | 40 | | | | | 45 | | |

| Asp | Cys | Ser | Asn | Ser | Ser | Ile | Val | Tyr | Glu | Ala | Ala | Asp | Val | Ile | Met |
| --- | --- | --- | --- | --- | --- | --- | --- | --- | --- | --- | --- | --- | --- | --- | --- |
| | 50 | | | | | 55 | | | | | 60 | | | | |

| His | Ala | Pro | Gly | Cys | Val | Pro | Cys | Val | Arg | Glu | Asn | Asn | Ser | Ser | Arg |
| --- | --- | --- | --- | --- | --- | --- | --- | --- | --- | --- | --- | --- | --- | --- | --- |
| 65 | | | | | 70 | | | | | 75 | | | | | 80 |

| Cys | Trp | Val | Ala | Leu | Thr | Pro | Thr | Leu | Ala | Ala | Arg | Asn | Ala | Ser | Val |
| --- | --- | --- | --- | --- | --- | --- | --- | --- | --- | --- | --- | --- | --- | --- | --- |
| | | | | 85 | | | | | 90 | | | | | 95 | |

| Pro | Thr | Thr | Thr | Leu | Arg | Arg | His | Val | Asp | Leu | Leu | Val | Gly | Thr | Ala |
| --- | --- | --- | --- | --- | --- | --- | --- | --- | --- | --- | --- | --- | --- | --- | --- |
| | | | 100 | | | | | 105 | | | | | 110 | | |

| Ala | Phe | Cys | Ser | Ala | Met | Tyr | Val | Gly | Asp | Leu | Cys | Gly | Ser | Val | Phe |
| --- | --- | --- | --- | --- | --- | --- | --- | --- | --- | --- | --- | --- | --- | --- | --- |
| | | 115 | | | | | 120 | | | | | 125 | | | |

| Leu | Ile | Ser | Gln | Leu | Phe | Thr | Phe | Ser | Pro | Arg | Arg | His | Glu | Thr | Val |
| --- | --- | --- | --- | --- | --- | --- | --- | --- | --- | --- | --- | --- | --- | --- | --- |
| | 130 | | | | | 135 | | | | | 140 | | | | |

| Gln | Asp | Cys | Asn | Cys | Ser | Ile | Tyr | Pro | Gly | His | Val | Ser | Gly | His | Arg |
| --- | --- | --- | --- | --- | --- | --- | --- | --- | --- | --- | --- | --- | --- | --- | --- |
| 145 | | | | | 150 | | | | | 155 | | | | | 160 |

| Met | Ala | Trp | Asp | Met | Met |
| --- | --- | --- | --- | --- | --- |
| | | | | 165 | |

( 2 ) INFORMATION FOR SEQ ID NO:33:

( i ) SEQUENCE CHARACTERISTICS:
        ( A ) LENGTH: 166 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:33:

| Leu | Glu | Asp | Gly | Val | Asn | Tyr | Ala | Thr | Gly | Asn | Leu | Pro | Gly | Cys | Ser |
| --- | --- | --- | --- | --- | --- | --- | --- | --- | --- | --- | --- | --- | --- | --- | --- |
| 1 | | | | 5 | | | | | 10 | | | | | 15 | |

```
       Phe   Ser   Ile   Phe   Leu   Leu   Ala   Leu   Leu   Ser   Cys   Leu   Thr   Val   Pro   Ala
                         20                            25                            30

Ser   Ala   Tyr   Gln   Val   Arg   Asn   Ser   Thr   Gly   Leu   Tyr   His   Val   Thr   Asn
                         35                            40                            45

Asp   Cys   Pro   Asn   Ser   Ser   Ile   Val   Tyr   Glu   Ala   His   Asp   Ala   Ile   Leu
             50                            55                            60

His   Thr   Pro   Gly   Cys   Val   Pro   Cys   Val   Arg   Glu   Gly   Asn   Val   Ser   Arg
       65                            70                            75                            80

Cys   Trp   Val   Ala   Met   Thr   Pro   Thr   Val   Ala   Thr   Arg   Asp   Gly   Arg   Leu
                               85                            90                            95

Pro   Ala   Thr   Gln   Leu   Arg   Arg   His   Ile   Asp   Leu   Leu   Val   Gly   Ser   Ala
                         100                           105                           110

Thr   Leu   Cys   Ser   Ala   Leu   Tyr   Val   Gly   Asp   Leu   Cys   Gly   Ser   Val   Phe
                   115                           120                     125

Leu   Ile   Gly   Gln   Leu   Phe   Thr   Phe   Ser   Pro   Arg   Arg   His   Trp   Thr   Thr
                   130                           135                     140

Gln   Gly   Cys   Asn   Cys   Ser   Ile   Tyr   Pro   Gly   His   Ile   Thr   Gly   His   Arg
       145                           150                           155                           160

Met   Ala   Trp   Asp   Met   Met
                               165
```

( 2 ) INFORMATION FOR SEQ ID NO:34:

( i ) SEQUENCE CHARACTERISTICS:
        ( A ) LENGTH: 166 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:34:

```
       Leu   Glu   Asp   Gly   Val   Asn   Tyr   Ala   Thr   Gly   Asn   Leu   Pro   Gly   Cys   Ser
       1                       5                             10                            15

Phe   Ser   Ile   Phe   Leu   Leu   Ala   Leu   Leu   Ser   Cys   Leu   Thr   Ile   Pro   Ala
                         20                            25                            30

Ser   Ala   Tyr   Glu   Val   Arg   Asn   Val   Ser   Gly   Ile   Tyr   His   Val   Thr   Asn
                         35                            40                            45

Asp   Cys   Ser   Asn   Ser   Ser   Ile   Val   Tyr   Glu   Ala   Ala   Asp   Met   Ile   Met
             50                            55                            60

His   Thr   Pro   Gly   Cys   Val   Pro   Cys   Val   Arg   Glu   Asp   Asn   Ser   Ser   Arg
       65                            70                            75                            80

Cys   Trp   Val   Ala   Leu   Thr   Pro   Thr   Leu   Ala   Ala   Arg   Asn   Ala   Ser   Val
                               85                            90                            95

Pro   Thr   Thr   Thr   Ile   Arg   Arg   His   Val   Asp   Leu   Leu   Val   Gly   Ala   Ala
                         100                           105                           110

Ala   Phe   Cys   Ser   Ala   Met   Tyr   Val   Gly   Asp   Leu   Cys   Gly   Ser   Val   Phe
                   115                           120                     125

Leu   Val   Ser   Gln   Leu   Phe   Thr   Phe   Ser   Pro   Arg   Arg   His   Glu   Thr   Val
                   130                           135                     140

Gln   Asp   Cys   Asn   Cys   Ser   Ile   Tyr   Pro   Gly   His   Leu   Ser   Gly   His   Arg
       145                           150                           155                           160

Met   Ala   Trp   Asp   Met   Met
                               165
```

( 2 ) INFORMATION FOR SEQ ID NO:35:

( i ) SEQUENCE CHARACTERISTICS:

(A) LENGTH: 1210 base pairs
(B) TYPE: nucleic acid
(C) STRANDEDNESS: single
(D) TOPOLOGY: linear (i i) MOLECULE TYPE: Other
(A) DESCRIPTION: cDNA to genomic RNA (x i) SEQUENCE DESCRIPTION: SEQ ID NO:35:

| | | | | | | |
|---|---|---|---|---|---|---|
| AATGGCTCAG | CTGCTCCGGA | TCCCACAAGC | CATCTTGGAC | ATGATCGCTG | GTGCTCACTG | 60 |
| GGGAGTCCTG | GCGGGCATAG | CGTATTTCTC | CATGGTGGGG | AACTGGGCGA | AGGTCCTGGT | 120 |
| AGTGCTGCTG | CTATTTGCCG | GCGTCGACGC | GGAAACCCAC | GTCACCGGGG | GAAGTGCCGG | 180 |
| CCACACTGTG | TCTGGATTTG | TTAGCCTCCT | CGCACCAGGC | GCCAAGCAGA | ACGTCCAGCT | 240 |
| GATCAACACC | AACGGCAGTT | GGCACCTCAA | TAGCACGGCT | CTGAACTGCA | ATGATAGCCT | 300 |
| TAACACCGGC | TGGTTGGCAG | GGCTTTTCTA | TCACCACAAG | TTCAACTCTT | CAGGCTGTCC | 360 |
| TGAGAGGCTA | GCCAGCTGCC | GACCCCTTAC | CGATTTTGAC | CAGGGCTGGG | GCCCTATCAG | 420 |
| TTATGCCAAC | GGAAGCGGCC | CCGACCAGCG | CCCCTACTGC | TGGCACTACC | CCCCAAAACC | 480 |
| TTGCGGTATT | GTGCCCGCGA | AGAGTGTGTG | TGGTCCGGTA | TATTGCTTCA | CTCCCAGCCC | 540 |
| CGTGGTGGTG | GGAACGACCG | ACAGGTCGGG | CGCGCCCACC | TACAGCTGGG | GTGAAAATGA | 600 |
| TACGGACGTC | TTCGTCCTTA | ACAATACCAG | GCCACCGCTG | GGCAATTGGT | TCGGTTGTAC | 660 |
| CTGGATGAAC | TCAACTGGAT | TCACCAAAGT | GTGCGGAGCG | CCTCCTTGTG | TCATCGGAGG | 720 |
| GGCGGGCAAC | AACACCCTGC | ACTGCCCCAC | TGATTGCTTC | CGCAAGCATC | CGGACGCCAC | 780 |
| ATACTCTCGG | TGCGGCTCCG | GTCCCTGGAT | CACACCCAGG | TGCCTGGTCG | ACTACCCGTA | 840 |
| TAGGCTTTGG | CATTATCCTT | GTACCATCAA | CTACACCATA | TTTAAAATCA | GGATGTACGT | 900 |
| GGGAGGGGTC | GAACACAGGC | TGGAAGCTGC | CTGCAACTGG | ACGCGGGGCG | AACGTTGCGA | 960 |
| TCTGGAAGAC | AGGGACAGGT | CCGAGCTCAG | CCCGTTACTG | CTGACCACTA | CACAGTGGCA | 1020 |
| GGTCCTCCCG | TGTTCCTTCA | CAACCCTACC | AGCCTTGTCC | ACCGGCCTCA | TCCACCTCCA | 1080 |
| CCAGAACATT | GTGGACGTGC | AGTACTTGTA | CGGGGTGGGG | TCAAGCATCG | CGTCCTGGGC | 1140 |
| CATTAAGTGG | GAGTACGTCG | TTCTCCTGTT | CCTTCTGCTT | GCAGACGCGC | GCGTCTGCTC | 1200 |
| CTGCTTGTGG | | | | | | 1210 |

(2) INFORMATION FOR SEQ ID NO:36:

(i) SEQUENCE CHARACTERISTICS:
(A) LENGTH: 541 base pairs
(B) TYPE: nucleic acid
(C) STRANDEDNESS: single
(D) TOPOLOGY: linear (i i) MOLECULE TYPE: Other
(A) DESCRIPTION: cDNA to genomic RNA (x i) SEQUENCE DESCRIPTION: SEQ ID NO:36:

| | | | | | | |
|---|---|---|---|---|---|---|
| AATGGCTCAG | CTGCTCCGCA | TCCCACAAGC | CATCTTGGAT | ATGATCGCTG | GTGCTCACTG | 60 |
| GGGAGTCCTG | GCGGGCATAG | CGTATTTCTC | CATGGTGGGG | AACTGGGCGA | AGGTCCTGGT | 120 |
| AGTGCTGTTG | CTGTTTGCCG | GCGTCGACGC | GGAAACCATC | GTCTCCGGGG | GACAAGCCGC | 180 |
| CCGCGCCATG | TCTGGACTTG | TTAGTCTCTT | CACACCAGGC | GCTAAGCAGA | ACATCCAGCT | 240 |
| GATCAACACC | AACGGCAGTT | GGCACATCAA | TAGCACGGCC | TTGAACTGCA | ATGAAAGCCT | 300 |
| TAACACCGGC | TGGTTAGCAG | GGCTTATCTA | TCAACACAAA | TTCAACTCTT | CGGGCTGTCC | 360 |
| CGAGAGGTTG | GCCAGCTGCC | GACGCCTTAC | CGATTTTGAC | CAGGGCTGGG | GCCCTATCAG | 420 |

5,879,904

37

38

-continued

| TCATGCCAAC | GGAAGCGGCC | CCGACCAACG | CCCCTATTGT | TGGCACTACC | CCCCAAAACC | 480 |
| TTGCGGTATC | GTGCCCGCAA | AGAGCGTATG | TGGCCCGGTA | TATTGCTTCA | CTCCCAGCCC | 540 |
| C | | | | | | 541 |

( 2 ) INFORMATION FOR SEQ ID NO:37:

( i ) SEQUENCE CHARACTERISTICS:
        ( A ) LENGTH: 541 base pairs
        ( B ) TYPE: nucleic acid
        ( C ) STRANDEDNESS: single
        ( D ) TOPOLOGY: linear ( i i ) MOLECULE TYPE: Other
        ( A ) DESCRIPTION: cDNA to genomic RNA ( x i ) SEQUENCE DESCRIPTION: SEQ ID NO:37:

| GGTGTCGCAG | TTGCTCCGGA | TCCCACAAGC | TGTCGTGGAC | ATGGTGGCGG | GGGCCCACTG | 60 |
| GGGAGTCCTG | GCGGGCCTTG | CCTACTATTC | CATGGTAGGG | AACTGGGCTA | AGGTCCTGAT | 120 |
| TGTGGCGCTA | CTCTTCGCCG | GCGTTGACGG | GGAGACCTAC | ACGTCGGGGG | GGGCGGCCAG | 180 |
| CCACACCACC | TCCACGCTCG | CGTCCCTCTT | CTCACCTGGG | GCGTCTCAGA | GAATCCAGCT | 240 |
| TGTGAATACC | AACGGCAGCT | GGCACATCAA | CAGGACTGCC | CTAAACTGCA | ATGACTCCCT | 300 |
| CCACACTGGG | TTCCTTGCCG | CGCTGTTCTA | CACACACAGG | TTCAACTCGT | CCGGGTGCCC | 360 |
| GGAGCGCATG | GCCAGCTGCC | GCCCCATTGA | CTGGTTCGCC | CAGGGATGGG | GCCCCATCAC | 420 |
| CTATACTGAG | CCTGACAGCC | CGGATCAGAG | GCCTTATTGC | TGGCATTACG | CGCCTCGACC | 480 |
| GTGTGGTATC | GTACCCGCGT | CGCAGGTGTG | TGGTCCAGTG | TATTGCTTCA | CCCCAAGCCC | 540 |
| T | | | | | | 541 |

( 2 ) INFORMATION FOR SEQ ID NO:38:

( i ) SEQUENCE CHARACTERISTICS:
        ( A ) LENGTH: 325 base pairs
        ( B ) TYPE: nucleic acid
        ( C ) STRANDEDNESS: single
        ( D ) TOPOLOGY: linear ( i i ) MOLECULE TYPE: Other
        ( A ) DESCRIPTION: cDNA to genomic RNA ( x i ) SEQUENCE DESCRIPTION: SEQ ID NO:38:

| GGTGTCGCAG | TTACTCCGGA | TCCCACAAGC | TGTCATGGAC | ATGGTGGCGG | GGGCCCACTG | 60 |
| GGGAGTCCTA | GCGGGCCTTG | CCTACTATTC | CATGGTGGGG | AACTGGGCTA | AGGTTTTGAT | 120 |
| TGTGATGCTA | CTCTTTGCCG | GCGTTGACGG | GCATACCCGC | GTGACGGGGG | GGGTGCAAGG | 180 |
| CCACGTCACC | TCTACACTCA | CGTCCCTCTT | TAGACCTGGG | GCGTCCAGA | AAATTCAGCT | 240 |
| TGTAAACACC | AATGGCAGTT | GGCATATCAA | CAGGACTGCC | CTGAACTGCA | ATGACTCCCT | 300 |
| CCAAACTGGG | TTCCTTGCCG | CGCTG | | | | 325 |

( 2 ) INFORMATION FOR SEQ ID NO:39:

( i ) SEQUENCE CHARACTERISTICS:
        ( A ) LENGTH: 403 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:39:

| | Met | Ala | Gln | Leu | Leu | Arg | Ile | Pro | Gln | Ala | Ile | Leu | Asp | Met | Ile | Ala |
| | 1 | | | | 5 | | | | | 10 | | | | | 15 | |

|       |       |       |       |       |       |       |       |       |       |       |       |       |       |       |
|-------|-------|-------|-------|-------|-------|-------|-------|-------|-------|-------|-------|-------|-------|-------|
| Gly   | Ala   | His   | Trp   | Gly   | Val   | Leu   | Ala   | Gly   | Ile   | Ala   | Tyr   | Phe   | Ser   | Met   | Val |
|       |       |       | 20    |       |       |       |       | 25    |       |       |       |       | 30    |       |     |
| Gly   | Asn   | Trp   | Ala   | Lys   | Val   | Leu   | Val   | Val   | Leu   | Leu   | Leu   | Phe   | Ala   | Gly   | Val |
|       |       | 35    |       |       |       |       | 40    |       |       |       |       | 45    |       |       |     |
| Asp   | Ala   | Glu   | Thr   | His   | Val   | Thr   | Gly   | Gly   | Ser   | Ala   | Gly   | His   | Thr   | Val   | Ser |
|       | 50    |       |       |       |       | 55    |       |       |       |       | 60    |       |       |       |     |
| Gly   | Phe   | Val   | Ser   | Leu   | Leu   | Ala   | Pro   | Gly   | Ala   | Lys   | Gln   | Asn   | Val   | Gln   | Leu |
| 65    |       |       |       |       | 70    |       |       |       |       | 75    |       |       |       |       | 80  |
| Ile   | Asn   | Thr   | Asn   | Gly   | Ser   | Trp   | His   | Leu   | Asn   | Ser   | Thr   | Ala   | Leu   | Asn   | Cys |
|       |       |       |       | 85    |       |       |       |       | 90    |       |       |       |       | 95    |     |
| Asn   | Asp   | Ser   | Leu   | Asn   | Thr   | Gly   | Trp   | Leu   | Ala   | Gly   | Leu   | Phe   | Tyr   | His   | His |
|       |       |       | 100   |       |       |       |       | 105   |       |       |       |       | 110   |       |     |
| Lys   | Phe   | Asn   | Ser   | Ser   | Gly   | Cys   | Pro   | Glu   | Arg   | Leu   | Ala   | Ser   | Cys   | Arg   | Pro |
|       |       | 115   |       |       |       |       | 120   |       |       |       |       | 125   |       |       |     |
| Leu   | Thr   | Asp   | Phe   | Asp   | Gln   | Gly   | Trp   | Gly   | Pro   | Ile   | Ser   | Tyr   | Ala   | Asn   | Gly |
|       | 130   |       |       |       |       | 135   |       |       |       |       | 140   |       |       |       |     |
| Ser   | Gly   | Pro   | Asp   | Gln   | Arg   | Pro   | Tyr   | Cys   | Trp   | His   | Tyr   | Pro   | Pro   | Lys   | Pro |
| 145   |       |       |       |       | 150   |       |       |       |       | 155   |       |       |       |       | 160 |
| Cys   | Gly   | Ile   | Val   | Pro   | Ala   | Lys   | Ser   | Val   | Cys   | Gly   | Pro   | Val   | Tyr   | Cys   | Phe |
|       |       |       |       | 165   |       |       |       |       | 170   |       |       |       |       | 175   |     |
| Thr   | Pro   | Ser   | Pro   | Val   | Val   | Val   | Gly   | Thr   | Thr   | Asp   | Arg   | Ser   | Gly   | Ala   | Pro |
|       |       |       | 180   |       |       |       |       | 185   |       |       |       |       | 190   |       |     |
| Thr   | Tyr   | Ser   | Trp   | Gly   | Glu   | Asn   | Asp   | Thr   | Asp   | Val   | Phe   | Val   | Leu   | Asn   | Asn |
|       |       | 195   |       |       |       |       | 200   |       |       |       |       | 205   |       |       |     |
| Thr   | Arg   | Pro   | Pro   | Leu   | Gly   | Asn   | Trp   | Phe   | Gly   | Cys   | Thr   | Trp   | Met   | Asn   | Ser |
|       | 210   |       |       |       |       | 215   |       |       |       |       | 220   |       |       |       |     |
| Thr   | Gly   | Phe   | Thr   | Lys   | Val   | Cys   | Gly   | Ala   | Pro   | Pro   | Cys   | Val   | Ile   | Gly   | Gly |
| 225   |       |       |       |       | 230   |       |       |       |       | 235   |       |       |       |       | 240 |
| Ala   | Gly   | Asn   | Asn   | Thr   | Leu   | His   | Cys   | Pro   | Thr   | Asp   | Cys   | Phe   | Arg   | Lys   | His |
|       |       |       |       | 245   |       |       |       |       | 250   |       |       |       |       | 255   |     |
| Pro   | Asp   | Ala   | Thr   | Tyr   | Ser   | Arg   | Cys   | Gly   | Ser   | Gly   | Pro   | Trp   | Ile   | Thr   | Pro |
|       |       |       | 260   |       |       |       |       | 265   |       |       |       |       | 270   |       |     |
| Arg   | Cys   | Leu   | Val   | Asp   | Tyr   | Pro   | Tyr   | Arg   | Leu   | Trp   | His   | Tyr   | Pro   | Cys   | Thr |
|       |       | 275   |       |       |       |       | 280   |       |       |       |       | 285   |       |       |     |
| Ile   | Asn   | Tyr   | Thr   | Ile   | Phe   | Lys   | Ile   | Arg   | Met   | Tyr   | Val   | Gly   | Gly   | Val   | Glu |
|       | 290   |       |       |       |       | 295   |       |       |       |       | 300   |       |       |       |     |
| His   | Arg   | Leu   | Glu   | Ala   | Ala   | Cys   | Asn   | Trp   | Thr   | Arg   | Gly   | Glu   | Arg   | Cys   | Asp |
| 305   |       |       |       |       | 310   |       |       |       |       | 315   |       |       |       |       | 320 |
| Leu   | Glu   | Asp   | Arg   | Asp   | Arg   | Ser   | Glu   | Leu   | Ser   | Pro   | Leu   | Leu   | Leu   | Thr   | Thr |
|       |       |       |       | 325   |       |       |       |       | 330   |       |       |       |       | 335   |     |
| Thr   | Gln   | Trp   | Gln   | Val   | Leu   | Pro   | Cys   | Ser   | Phe   | Thr   | Thr   | Leu   | Pro   | Ala   | Leu |
|       |       |       | 340   |       |       |       |       | 345   |       |       |       |       | 350   |       |     |
| Ser   | Thr   | Gly   | Leu   | Ile   | His   | Leu   | His   | Gln   | Asn   | Ile   | Val   | Asp   | Val   | Gln   | Tyr |
|       |       | 355   |       |       |       |       | 360   |       |       |       |       | 365   |       |       |     |
| Leu   | Tyr   | Gly   | Val   | Gly   | Ser   | Ser   | Ile   | Ala   | Ser   | Trp   | Ala   | Ile   | Lys   | Trp   | Glu |
|       |       | 370   |       |       |       |       | 375   |       |       |       |       | 380   |       |       |     |
| Tyr   | Val   | Val   | Leu   | Leu   | Phe   | Leu   | Leu   | Leu   | Ala   | Asp   | Ala   | Arg   | Val   | Cys   | Ser |
| 385   |       |       |       |       | 390   |       |       |       |       | 395   |       |       |       |       | 400 |
| Cys   | Leu   | Trp   |       |       |       |       |       |       |       |       |       |       |       |       |     |

( 2 ) INFORMATION FOR SEQ ID NO:40:

( i ) SEQUENCE CHARACTERISTICS:
        ( A ) LENGTH: 180 amino acids (B) TYPE: amino acid
(D) TOPOLOGY: linear (i i) MOLECULE TYPE: peptide (x i) SEQUENCE DESCRIPTION: SEQ ID NO:40:

| Met | Ala | Gln | Leu | Leu | Arg | Ile | Pro | Gln | Ala | Ile | Leu | Asp | Met | Ile | Ala |
|---|---|---|---|---|---|---|---|---|---|---|---|---|---|---|---|
| 1 | | | | 5 | | | | | 10 | | | | | 15 | |
| Gly | Ala | His | Trp | Gly | Val | Leu | Ala | Gly | Ile | Ala | Tyr | Phe | Ser | Met | Val |
| | | | 20 | | | | | 25 | | | | | 30 | | |
| Gly | Asn | Trp | Ala | Lys | Val | Leu | Val | Val | Leu | Leu | Leu | Phe | Ala | Gly | Val |
| | | 35 | | | | | 40 | | | | | 45 | | | |
| Asp | Ala | Glu | Thr | Ile | Val | Ser | Gly | Gln | Ala | Ala | Arg | Ala | Met | Ser | |
| | 50 | | | | | 55 | | | | | 60 | | | | |
| Gly | Leu | Val | Ser | Leu | Phe | Thr | Pro | Gly | Ala | Lys | Gln | Asn | Ile | Gln | Leu |
| 65 | | | | | 70 | | | | | 75 | | | | | 80 |
| Ile | Asn | Thr | Asn | Gly | Ser | Trp | His | Ile | Asn | Ser | Thr | Ala | Leu | Asn | Cys |
| | | | | 85 | | | | | 90 | | | | | 95 | |
| Asn | Glu | Ser | Leu | Asn | Thr | Gly | Trp | Leu | Ala | Gly | Leu | Ile | Tyr | Gln | His |
| | | | 100 | | | | | 105 | | | | | 110 | | |
| Lys | Phe | Asn | Ser | Ser | Gly | Cys | Pro | Glu | Arg | Leu | Ala | Ser | Cys | Arg | Arg |
| | | 115 | | | | | 120 | | | | | 125 | | | |
| Leu | Thr | Asp | Phe | Asp | Gln | Gly | Trp | Gly | Pro | Ile | Ser | His | Ala | Asn | Gly |
| | | 130 | | | | | 135 | | | | | 140 | | | |
| Ser | Ala | Pro | Asp | Gln | Arg | Pro | Tyr | Cys | Trp | His | Tyr | Pro | Pro | Lys | Pro |
| 145 | | | | | 150 | | | | | 155 | | | | | 160 |
| Cys | Gly | Ile | Val | Pro | Ala | Lys | Ser | Val | Cys | Gly | Pro | Val | Tyr | Cys | Phe |
| | | | | 165 | | | | | 170 | | | | | 175 | |
| Thr | Pro | Ser | Pro | | | | | | | | | | | | |
| | | | 180 | | | | | | | | | | | | |

(2) INFORMATION FOR SEQ ID NO:41:

(i) SEQUENCE CHARACTERISTICS:
(A) LENGTH: 180 amino acids
(B) TYPE: amino acid
(D) TOPOLOGY: linear (i i) MOLECULE TYPE: peptide (x i) SEQUENCE DESCRIPTION: SEQ ID NO:41:

| Val | Ser | Gln | Leu | Leu | Arg | Ile | Pro | Gln | Ala | Val | Val | Asp | Met | Val | Ala |
|---|---|---|---|---|---|---|---|---|---|---|---|---|---|---|---|
| 1 | | | | 5 | | | | | 10 | | | | | 15 | |
| Gly | Ala | His | Trp | Gly | Val | Leu | Ala | Gly | Leu | Ala | Tyr | Tyr | Ser | Met | Val |
| | | | 20 | | | | | 25 | | | | | 30 | | |
| Gly | Asn | Trp | Ala | Lys | Val | Leu | Ile | Val | Ala | Leu | Leu | Phe | Ala | Gly | Val |
| | | 35 | | | | | 40 | | | | | 45 | | | |
| Asp | Gly | Glu | Thr | Tyr | Thr | Ser | Gly | Gly | Ala | Ala | Ser | His | Thr | Thr | Ser |
| | 50 | | | | | 55 | | | | | 60 | | | | |
| Thr | Leu | Ala | Ser | Leu | Phe | Ser | Pro | Gly | Ala | Ser | Gln | Arg | Ile | Gln | Leu |
| 65 | | | | | 70 | | | | | 75 | | | | | 80 |
| Val | Asn | Thr | Asn | Gly | Ser | Trp | His | Ile | Asn | Arg | Thr | Ala | Leu | Asn | Cys |
| | | | | 85 | | | | | 90 | | | | | 95 | |
| Asn | Asp | Ser | Leu | His | Thr | Gly | Phe | Leu | Ala | Ala | Leu | Phe | Tyr | Thr | His |
| | | | 100 | | | | | 105 | | | | | 110 | | |
| Arg | Phe | Asn | Ser | Ser | Gly | Cys | Pro | Glu | Arg | Met | Ala | Ser | Cys | Arg | Pro |
| | | 115 | | | | | 120 | | | | | 125 | | | |

```
          Ile Asp Trp Phe Ala Gln Gly Trp Gly Pro Ile Thr Tyr Thr Glu Pro
              130                 135                 140

Asp Ser Pro Asp Gln Arg Pro Tyr Cys Trp His Tyr Ala Pro Arg Pro
          145                 150                 155                 160

Cys Gly Ile Val Pro Ala Ser Gln Val Cys Gly Pro Val Tyr Cys Phe
                          165                 170                 175

Thr Pro Ser Pro
                      180
```

( 2 ) INFORMATION FOR SEQ ID NO:42:

( i ) SEQUENCE CHARACTERISTICS:
        ( A ) LENGTH: 108 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:42:

```
          Val Ser Gln Leu Leu Arg Ile Pro Gln Ala Val Met Asp Met Val Ala
          1               5                   10                  15

Gly Ala His Trp Gly Val Leu Ala Gly Leu Ala Tyr Tyr Ser Met Val
                          20                  25                  30

Gly Asn Trp Ala Lys Val Leu Ile Val Met Leu Leu Phe Ala Gly Val
                      35                  40                  45

Asp Gly His Thr Arg Val Thr Gly Gly Val Gln Gly His Val Thr Ser
                  50                  55                  60

Thr Leu Thr Ser Leu Phe Arg Pro Gly Ala Ser Gln Lys Ile Gln Leu
          65                  70                  75                  80

Val Asn Thr Asn Gly Ser Trp His Ile Asn Arg Thr Ala Leu Asn Cys
                          85                  90                  95

Asn Asp Ser Leu Gln Thr Gly Phe Leu Ala Ala Leu
                          100                 105
```

( 2 ) INFORMATION FOR SEQ ID NO:43:

( i ) SEQUENCE CHARACTERISTICS:
        ( A ) LENGTH: 943 base pairs
        ( B ) TYPE: nucleic acid
        ( C ) STRANDEDNESS: single
        ( D ) TOPOLOGY: linear ( i i ) MOLECULE TYPE: Other
        ( A ) DESCRIPTION: cDNA to genomic RNA ( x i ) SEQUENCE DESCRIPTION: SEQ ID NO:43:

```
ACAATACGTG  TGTCACCCAG  ACAGTCGATT  TCAGCCTTGA  CCCTACCTTC  ACCATTGAGA        60

CAATCACGCT  CCCCCAGGAT  GCTGTCTCCC  GCACTCAACG  TCGGGGCAGG  ACTGGCAGGG       120

GGAAGCCAGG  CATCTACAGA  TTTGTGGCAC  CGGGGGAGCG  CCCCTCCGGC  ATGTTCGACT       180

CGTCCGTCCT  CTGTGAGTGC  TATGACGCAG  GCTGTGCTTG  GTATGAGCTC  ACGCCCGCCG       240

AGACTACAGT  TAGGCTACGA  GCGTACATGA  ACACCCCGGG  GCTTCCCGTG  TGCCAGGACC       300

ATCTTGAATT  TTGGGAGGGC  GTCTTTACAG  GCCTCACTCA  TATAGATGCC  CACTTTCTAT       360

CCCAGACAAA  GCAGAGTGGG  GAGAACCTTC  CTTACCTGGT  AGCGTACCAA  GCCACCGTGT       420

GCGCTAGGGC  TCAAGCCCCT  CCCCCATCGT  GGGACCAGAT  GTGGAAGTGT  TTGATTCGCC       480

TCAAGCCCAC  CCTCCATGGG  CCAACACCCC  TGCTATACAG  ACTGGGCGCT  GTTCAGAATG       540

AAATCACCCT  GACGCACCCA  GTCACCAAAT  ACATCATGAC  ATGCATGTCG  GCCGACCTGG       600

AGGTCGTCAC  GAGCACCTGG  GTGCTCGTTG  GCGGCGTCCT  GGCTGCTTTG  GCCGCGTATT       660
```

-continued

| | | | | |
|---|---|---|---|---|
| GCCTGTCAAC | AGGCTGCGTG | GTCATAGTGG | GCAGGGTCGT | CTTGTCCGGG | AAGCCGGCAA | 720 |
| TCATACCTGA | CAGGGAAGTC | CTCTACCGAG | AGTTCGATGA | GATGGAAGAG | TGCTCTCAGC | 780 |
| ACTTACCGTA | CATCGAGCAA | GGGATGATGC | TCGCCGAGCA | GTTCAAGCAG | AAGGCCCTCG | 840 |
| GCCTCCTGCA | GACCGCGTCC | CGTCAGGCAG | AGGTTATCGC | CCCTGCTGTC | CAGACCAACT | 900 |
| GGCAAAAACT | CGAGACCTTC | TGGGCGAAGC | ATATGTGGAA | CTT | | 943 |

(2) INFORMATION FOR SEQ ID NO:44:

(i) SEQUENCE CHARACTERISTICS:
    (A) LENGTH: 569 base pairs
    (B) TYPE: nucleic acid
    (C) STRANDEDNESS: single
    (D) TOPOLOGY: linear (ii) MOLECULE TYPE: Other
    (A) DESCRIPTION: cDNA to genomic RNA (xi) SEQUENCE DESCRIPTION: SEQ ID NO:44:

| | | | | | |
|---|---|---|---|---|---|
| GTAACACATG | TGTCACTCAG | ACGGTCGATT | TCAGCTTGGA | TCCCACTCTC | ACCATCGAGA | 60 |
| CGACGACCGT | GCCCCAAGAT | GCGGTTTCGC | GCACGCAGCG | GCGAGGTAGG | ACTGGCAGGG | 120 |
| GCAGGAGAGG | CATCTATAGG | TTTGTGACTC | CAGGAGAACG | GCCCTCGGCG | ATGTTCGATT | 180 |
| CTTCGGTCCT | ATGTGAGTGT | TATGACGCGG | GCTGTGCTTG | GTATGAGCTC | ACGCCCGCTG | 240 |
| AGACCTCGGT | TAGGTTGCGG | GCTTACCTAA | ATACACCAGG | GTTGCCCGTC | TGCCAGGACC | 300 |
| ATCTGGAGTT | CTGGGAGAGC | GTCTTCACAG | GCCTCACCCA | CATAGACGCC | CACTTCTTGT | 360 |
| CCCAGACTAA | GCAGGCAGGA | GACAACTTCC | CCTACCTGGT | AGCATACCAA | GCCACAGTGT | 420 |
| GCGCCAGGGC | TAAGGCTCCA | CCTCCATCGT | GGGATCAAAT | GTGGAAGTGT | CTCATACGGC | 480 |
| TAAAGCCTAC | GCTGCACGGG | CCAACGCCCC | TGCTGTATAG | GCTAGGAGCC | GTCCAGAATG | 540 |
| AGGTCACCCT | CACACACCCT | ATAACCAAA | | | | 569 |

(2) INFORMATION FOR SEQ ID NO:45:

(i) SEQUENCE CHARACTERISTICS:
    (A) LENGTH: 313 amino acids
    (B) TYPE: amino acid
    (D) TOPOLOGY: linear (ii) MOLECULE TYPE: peptide (xi) SEQUENCE DESCRIPTION: SEQ ID NO:45:

```
Asn Thr Cys Val Thr Gln Thr Val Asp Phe Ser Leu Asp Pro Thr Phe
 1               5                  10                 15
Thr Ile Glu Thr Ile Thr Leu Pro Gln Asp Ala Val Ser Arg Thr Gln
            20                  25                  30
Arg Arg Gly Arg Thr Gly Arg Gly Lys Pro Gly Ile Tyr Arg Phe Val
        35                  40                  45
Ala Pro Gly Glu Arg Pro Ser Gly Met Phe Asp Ser Ser Val Leu Cys
    50                  55                  60
Glu Cys Tyr Asp Ala Gly Cys Ala Trp Tyr Glu Leu Thr Pro Ala Glu
65                  70                  75                  80
Thr Thr Val Arg Leu Arg Ala Tyr Met Asn Thr Pro Gly Leu Pro Val
                85                  90                  95
Cys Gln Asp His Leu Glu Phe Trp Glu Gly Val Phe Thr Gly Leu Thr
            100                 105                 110
His Ile Asp Ala His Phe Leu Ser Gln Thr Lys Gln Ser Gly Glu Asn
        115                 120                 125
```

|     |     |     |     |     |     |     |     |     |     |     |     |     |     |     |
|---|---|---|---|---|---|---|---|---|---|---|---|---|---|---|
| Leu | Pro<br>130 | Tyr | Leu | Val | Ala | Tyr<br>135 | Gln | Ala | Thr | Val | Cys<br>140 | Ala | Arg | Ala | Gln |
| Ala<br>145 | Pro | Pro | Pro | Ser | Trp<br>150 | Asp | Gln | Met | Trp | Lys<br>155 | Cys | Leu | Ile | Arg | Leu<br>160 |
| Lys | Pro | Thr | Leu | His<br>165 | Gly | Pro | Thr | Pro | Leu<br>170 | Leu | Tyr | Arg | Leu | Gly<br>175 | Ala |
| Val | Gln | Asn | Glu<br>180 | Ile | Thr | Leu | Thr | His<br>185 | Pro | Val | Thr | Lys | Tyr<br>190 | Ile | Met |
| Thr | Cys | Met<br>195 | Ser | Ala | Asp | Leu | Glu<br>200 | Val | Val | Thr | Ser<br>205 | Thr | Trp | Val | Leu |
| Val | Gly<br>210 | Gly | Val | Leu | Ala | Ala<br>215 | Leu | Ala | Ala | Tyr | Cys<br>220 | Leu | Ser | Thr | Gly |
| Cys<br>225 | Val | Val | Ile | Val | Gly<br>230 | Arg | Val | Val | Leu | Ser<br>235 | Gly | Lys | Pro | Ala | Ile<br>240 |
| Ile | Pro | Asp | Arg | Glu<br>245 | Val | Leu | Tyr | Arg | Glu<br>250 | Phe | Asp | Glu | Met | Glu<br>255 | Glu |
| Cys | Ser | Gln | His<br>260 | Leu | Pro | Tyr | Ile | Glu<br>265 | Gln | Gly | Met | Met | Leu<br>270 | Ala | Glu |
| Gln | Phe | Lys<br>275 | Gln | Lys | Ala | Leu | Gly<br>280 | Leu | Leu | Gln | Thr | Ala<br>285 | Ser | Arg | Gln |
| Ala | Glu<br>290 | Val | Ile | Ala | Pro | Ala<br>295 | Val | Glu | Thr | Asn | Trp<br>300 | Gln | Lys | Leu | Glu |
| Thr<br>305 | Phe | Trp | Ala | Lys | His<br>310 | Met | Trp | Asn |     |     |     |     |     |     |     |

( 2 ) INFORMATION FOR SEQ ID NO:46:

( i ) SEQUENCE CHARACTERISTICS:
        ( A ) LENGTH: 189 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:46:

|     |     |     |     |     |     |     |     |     |     |     |     |     |     |     |     |
|---|---|---|---|---|---|---|---|---|---|---|---|---|---|---|---|
| Asn<br>1 | Thr | Cys | Val | Thr<br>5 | Gln | Thr | Val | Asp | Phe<br>10 | Ser | Leu | Asp | Pro | Thr<br>15 | Leu |
| Thr | Ile | Glu | Thr<br>20 | Thr | Thr | Val | Pro | Gln<br>25 | Asp | Ala | Val | Ser | Arg<br>30 | Thr | Gln |
| Arg | Arg | Gly<br>35 | Arg | Thr | Gly | Arg<br>40 | Gly | Arg | Arg | Gly | Ile<br>45 | Tyr | Arg | Phe | Val |
| Thr | Pro<br>50 | Gly | Glu | Arg | Pro<br>55 | Ser | Ala | Met | Phe | Asp<br>60 | Ser | Ser | Val | Leu | Cys |
| Glu<br>65 | Cys | Tyr | Asp | Ala | Gly<br>70 | Cys | Ala | Trp | Tyr | Glu<br>75 | Leu | Thr | Pro | Ala | Glu<br>80 |
| Thr | Ser | Val | Arg | Leu<br>85 | Arg | Ala | Tyr | Leu | Asn<br>90 | Thr | Pro | Gly | Leu | Pro<br>95 | Val |
| Cys | Gln | Asp | His<br>100 | Leu | Glu | Phe | Trp | Glu<br>105 | Ser | Val | Phe | Thr | Gly<br>110 | Leu | Thr |
| His | Ile | Asp | Ala<br>115 | His | Phe | Leu | Ser | Gln<br>120 | Thr | Lys | Gln | Ala | Gly<br>125 | Asp | Asn |
| Phe | Pro<br>130 | Tyr | Leu | Val | Ala | Tyr<br>135 | Gln | Ala | Thr | Val | Cys<br>140 | Ala | Arg | Ala | Lys |
| Ala<br>145 | Pro | Pro | Pro | Ser | Trp<br>150 | Asp | Gln | Met | Trp | Lys<br>155 | Cys | Leu | Ile | Arg | Leu<br>160 |

| Lys | Pro | Thr | Leu | His<br>165 | Gly | Pro | Thr | Pro | Leu<br>170 | Leu | Tyr | Arg | Leu | Gly<br>175 | Ala |
| Val | Gln | Asn | Glu<br>180 | Val | Thr | Leu | Thr | His<br>185 | Pro | Ile | Thr | Lys | | | |

We claim:

1. An oligonucleotide encoding a peptide, wherein said peptide is an amino acid (aa) sequence selected from the group consisting of:

$aa_{58}$ to $aa_{66}$ of SEQ ID NO:3;
$aa_{49}$ to $aa_{78}$ of SEQ ID NO:5;
$aa_{123}$ to $aa_{133}$ of SEQ ID NO:5;
SEQ ID NO:3;
SEQ ID NO:5; and
SEQ ID NO:7.

2. An oligonucleotide encoding a peptide, wherein said oligonucleotide is a DNA sequence selected from the group consisting of:

a) n177 to n202 of SEQ ID NO:2;
b) n233 to n247 of SEQ ID NO:2;
c) n254 to n272 of SEQ ID NO:2;
d) n272 to n288 of SEQ ID NO:2;
e) n156 to n170 of SEQ ID NO:4;
f) n170 to n217 of SEQ ID NO:4;
g) n310 to n334 of SEQ ID NO:4;
h) SEQ ID NO:2;
i) SEQ ID NO:4; and
j) SEQ ID NO:6.

3. An oligonucleotide encoding a peptide, wherein said oligonucleotide is a DNA sequence selected from the group consisting of a) n118 to n138 of SEQ ID NO:2; and
b) n267 to n283 of SEQ ID NO:4.

4. An oligonucleotide probe comprising a DNA molecule according to any one of claims 1, 2, or 3, wherein said DNA molecule is labeled.

5. An expression vector comprising a DNA molecule or oligonucleotide as claimed in any one of claims 1, 2, or 3.

6. Host transformed with a vector according to claim 5.

7. Analytical kit for the detection of nucleotide sequences of the hepatitis C virus comprising one or more polynucleotide probe(s) according to claim 4.

8. A process for preparing a polypeptide comprising:

inserting a DNA molecule as claimed in any one of claims 1, 2, or 3, encoding the polypeptide into an expression vector; transforming cells with this expression vector comprising said inserted DNA molecule; and culturing said transformed cells.

* * * * *